United States Patent
Tornier et al.

(10) Patent No.: US 9,364,242 B2
(45) Date of Patent: Jun. 14, 2016

(54) DRILLING DEVICE FOR FORMING A CURVED OSSEOUS CHANNEL WITHIN THE BODY OF A VERTEBRA

(75) Inventors: Alain Tornier, Saint-Ismier (FR); Guy Viart, Saint-Leger (FR); Jean-Yves Leroy, Campagne les Hesdin (FR); Adrien Billon, Ronchin (FR); Afshin Gangi, Strasbourg (FR); Orlando Ortiz, New York, NY (US)

(73) Assignee: CLARIANCE, Dainville (FR)

( * ) Notice: Subject to any disclaimer, the term of this patent is extended or adjusted under 35 U.S.C. 154(b) by 837 days.

(21) Appl. No.: 13/029,141

(22) Filed: Feb. 17, 2011

(65) Prior Publication Data
US 2012/0191094 A1   Jul. 26, 2012

(30) Foreign Application Priority Data
Jan. 24, 2011   (FR) ...................................... 11 00199

(51) Int. Cl.
*A61B 17/16* (2006.01)
*A61B 17/17* (2006.01)
*A61B 17/00* (2006.01)

(52) U.S. Cl.
CPC ......... *A61B 17/1671* (2013.01); *A61B 17/1637* (2013.01); *A61B 17/1642* (2013.01); *A61B 17/1631* (2013.01); *A61B 17/1697* (2013.01); *A61B 17/1757* (2013.01); *A61B 2017/00862* (2013.01)

(58) Field of Classification Search
USPC ........... 606/79–80, 86 R, 87–89, 96–99, 104; 269/309–310
See application file for complete search history.

(56) References Cited

U.S. PATENT DOCUMENTS

| | | | | |
|---|---|---|---|---|
| 4,828,221 A * | 5/1989 | Scobie | ...................... | F16K 1/22 251/308 |
| 5,488,761 A * | 2/1996 | Leone | .................. | A61B 17/164 29/2.1 |
| 6,053,922 A * | 4/2000 | Krause | ................. | A61B 17/164 464/78 |
| 6,074,392 A * | 6/2000 | Durham | .................. | A61B 17/68 606/62 |
| 6,447,518 B1 * | 9/2002 | Krause et al. | .................... | 606/80 |
| 7,105,003 B2 * | 9/2006 | Hiltebrandt | ...... | A61B 17/32002 606/159 |
| 7,241,297 B2 * | 7/2007 | Shaolian et al. | ................. | 606/80 |
| 2006/0195094 A1 * | 8/2006 | McGraw et al. | ................ | 606/61 |
| 2010/0211076 A1 * | 8/2010 | Germain et al. | ................ | 606/84 |
| 2010/0268279 A1 * | 10/2010 | Gabelberger et al. | ......... | 606/278 |

FOREIGN PATENT DOCUMENTS

WO    WO 2008/100484    *   8/2008    ............. A61B 17/32

* cited by examiner

*Primary Examiner* — Anu Ramana
*Assistant Examiner* — Jessica Weiss
(74) *Attorney, Agent, or Firm* — Young & Thompson

(57) ABSTRACT

The drilling device for forming an osseous channel (2) with a curved profile (2b) via a straight cannula (6) previously fixed in the body of a vertebra (3) with a cortical plateau (4) of a spinal segment (Sr) of a vertebral column (Cv) includes a guide pin (8) which is provided from a guide pin kit and has at one of its ends a curved profile (8a) of which the radius of curvature R is less than 20 millimeters, and a sharpened tip (8b) arranged in a direction defined by an angle Y which is less than 90 degrees to the longitudinal axis of said pin, the profile of said guide pin (8) making it possible to define, after insertion thereof into the body of the vertebra (3), two contact points a and b ensuring the guidance of the free end of an articulated drill bit (10) so as to position said free end in a direction substantially perpendicular to that of the cortical plateau (4) of the vertebra (3) to be drilled.

24 Claims, 28 Drawing Sheets

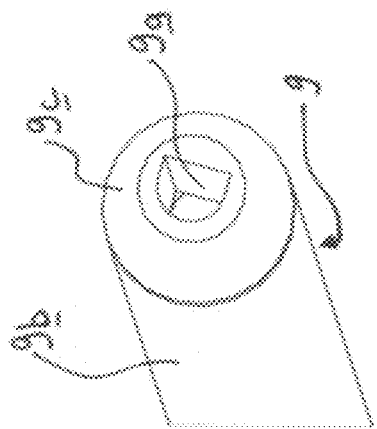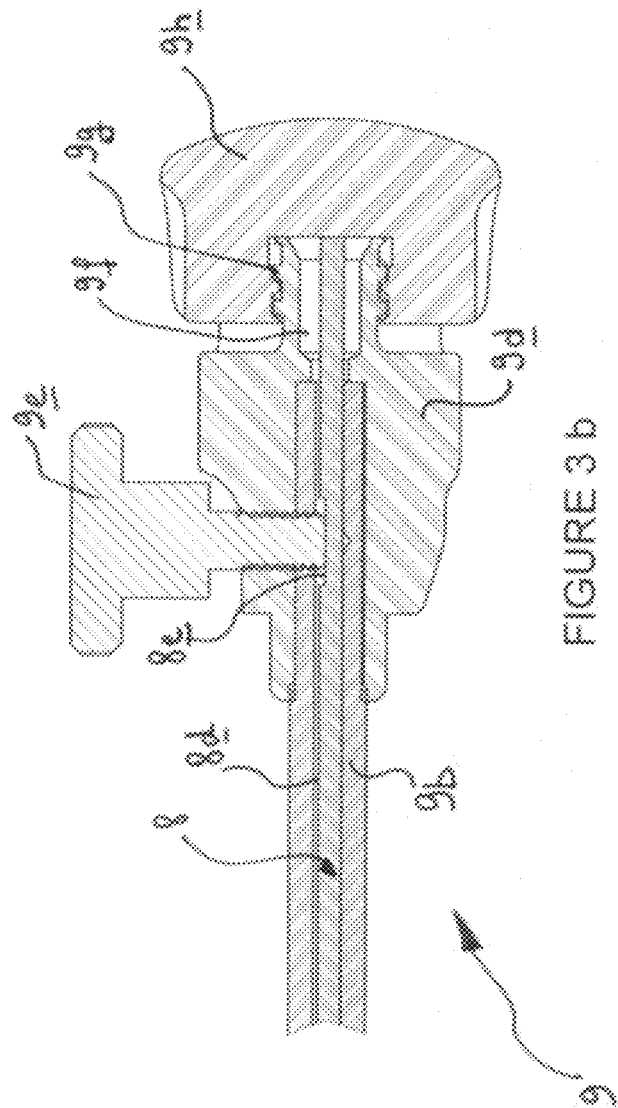

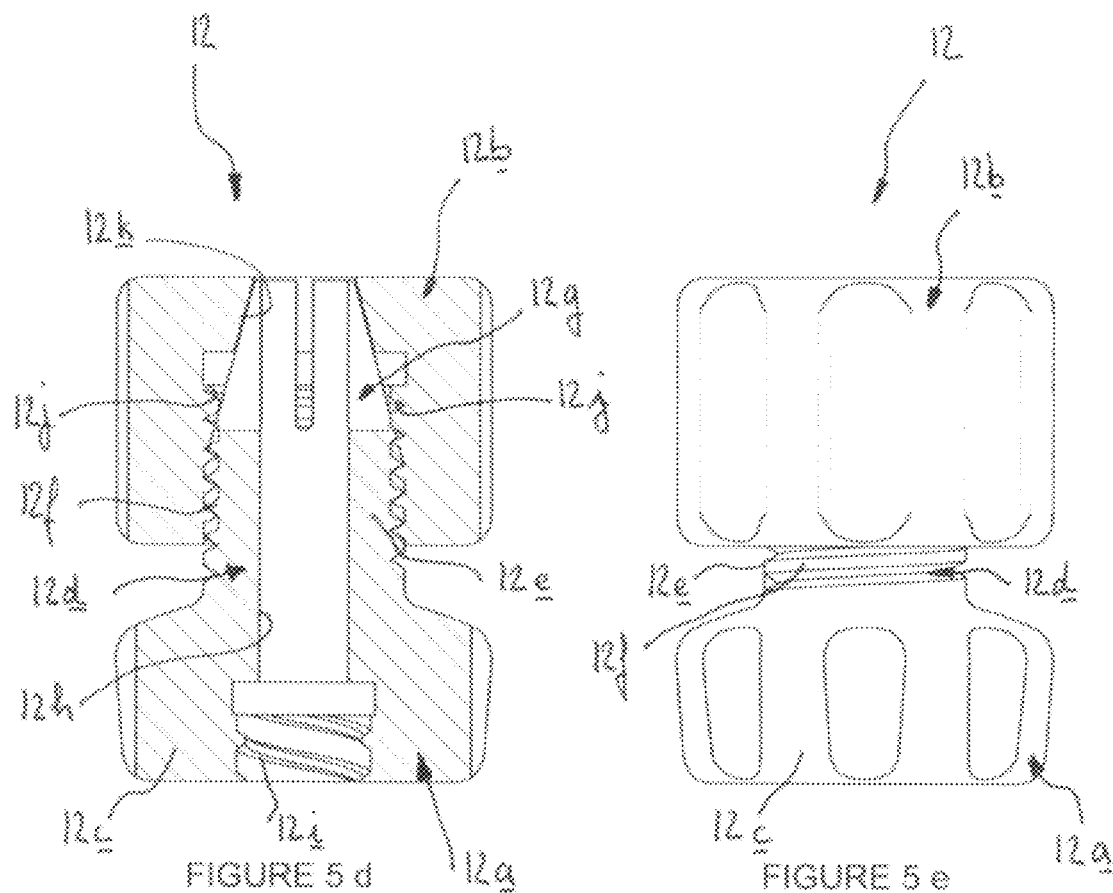

DRILLING DEVICE FOR FORMING A CURVED OSSEOUS CHANNEL WITHIN THE BODY OF A VERTEBRA

FIELD OF THE INVENTION

The present invention relates to a drilling device for forming a curved osseous channel within a the body of a vertebra and, in particular, for enabling access to the intervertebral disc and the insertion of a nucleic implant between the overlying and underlying vertebral bodies of a spinal segment to be manipulated.

SUMMARY OF THE INVENTION

The object of the drilling device according to the present invention is to improve the means which make it possible to form a curved osseous channel, in such a way that said channel always finishes in a direction substantially perpendicular to that of the cortical plateau of the vertebra to be drilled.

The direction of the curved osseous channel must make it possible to insert tools ensuring nucleotomy in the intervertebral disc.

The drilling device according to the present invention comprises a guide pin which is provided from a guide pin kit and has at one of its ends on the one hand a curved profile of which the radius of curvature R is less than 20 millimeters, and on the other hand a sharpened tip arranged in a direction defined by an angle Y which is less than 90 degrees to the longitudinal axis of said pin, the profile of said guide pin making it possible to define, after insertion thereof into the body of the vertebra, two contact points a and b ensuring the guidance of the free end of an articulated drill bit so as to position said free end in a direction substantially perpendicular to that of the cortical plateau of the vertebra to be drilled.

The drilling device according to the present invention comprises a first contact point a which is defined by the tangent to the outer profile of the radius of curvature R of the guide pin which is perpendicular to the cortical plateau of the vertebra, and a second contact point b which is defined by the free end of the articulated drill bit which rests against the inner profile of the sharpened tip of the guide pin arranged within the depth of the cortical plateau of the vertebra.

The drilling device according to the present invention comprises a guide pin which is made of a material which is both hard-wearing and flexible, such as a Superelastic Nitinol alloy.

The drilling device according to the present invention comprises a guide pin of which the outer diameter is less than 3 millimeters.

The drilling device according to the present invention comprises a guide pin of which the outer diameter is between 1.4 millimeters and 2 millimeters.

The drilling device according to the present invention comprises a guide pin of which the curved profile has a radius of curvature R which is between 10 millimeters and 20 millimeters.

The drilling device according to the present invention has an angle Y of the sharpened tip which is between 70 and 85 degrees.

The drilling device according to the present invention has a guide pin comprising a straight longitudinal portion having a flattened part which cooperates with a complementary profile formed in a pin holder, making it possible to ensure on the one hand that the guide pin is blocked against rotation inside the pin holder, and on the other hand that said guide pin is rigidified over its straight longitudinal portion during insertion of said guide pin and of said pin holder through a straight cannula previously fixed in the body of the vertebra.

The drilling device according to the present invention has a guide pin comprising, at its end opposite that with a curved profile, a notch formed over the periphery of the straight longitudinal portion and, more specifically, beside the flattened part, said notch cooperating with a tensioning screw guided in a grasping grip for of the pin holder for blocking the movement in translation of said guide pin in said pin holder.

The drilling device according to the present invention comprises a pin holder which is formed of a metal cylindrical tube formed in one piece at one of its ends with a grasping grip equipped with a tensioning screw and a hollow cylindrical sleeve having, over its outer profile, a fast thread making it possible to screw in a plug making it possible to block the movement in translation of the guide pin relative to the pin holder.

The drilling device according to the present invention comprises an articulated drill bit which is formed of a metal cylindrical tube comprising, at one of its ends, a grasping grip, whereas the other end is cropped on the one hand in accordance with a profile ensuring deformation and articulation along a curved shape of said end, and on the other so as to define a cutting end comprising a first set of teeth arranged over the periphery of said tube and a second set of teeth arranged at the end of the metal tube and a protective sheath arranged in the inner portion of the metal tube, said protective sheath being made of a resilient material making it possible to internally smooth the irregularities and gaps in the free end arising from the profile.

The drilling device according to the present invention comprises an articulated drill bit, of which the grasping grip comprises in the extension of the metal tube a hollow cylindrical sleeve having, over its outer profile, a fast thread which makes it possible to insert and fix a centering sheath inside said metal tube.

The drilling device according to the present invention comprises a protective sheath which is made of a resilient material ensuring a significant coefficient of slip for the sliding of the guide pin and/or of the centering sheath during drilling of the curved osseous channel.

The drilling device according to the present invention comprises an articulated drill bit, of which the profile of the metal cylindrical tube is formed by a sequence of alternately concave and convex loops ensuring deformation and articulation of the end of the articulated drill bit in a curved shape.

The drilling device according to the present invention comprises an articulated drill bit of which the cutting edge of each tooth of the first set of teeth is slightly inclined relative to the longitudinal axis of the articulated drill bit.

The drilling device according to the present invention comprises an articulated drill bit of which the cutting edge of each tooth of the second set of teeth is sharply inclined so as to intersect the longitudinal axis of the articulated drill bit.

The drilling device according to the present invention comprises a centering sheath which is formed of a cylindrical tube made of a resilient material and is formed in one piece at one of its ends with a grasping head comprising, on the one hand, an inner threaded bore for cooperation with the sleeve of the grip of the articulated drill bit for immobilisation of said sleeve on said articulated drill bit and, on the other, a blocking device opposite the inner threaded bore making it possible, by pinching, to block the movement in translation of the cylindrical tube inside said head of the centering sheath.

The drilling device according to the present invention comprises an articulated drill bit comprising a locking device arranged on the metal tube and beneath the grasping grip so as to immobilise said drill bit, by means of a retaining element and a fixing nut, on the straight cannula previously fixed in the body of the vertebra.

The drilling device according to the present invention comprises a locking device which is formed of a retaining element comprising a cylindrical head formed in one piece with a sleeve having a cylindrical outer profile equipped with a thread extending via a split, conical outer profile.

The drilling device according to the present invention comprises a locking device of which the retaining element is perforated through its middle by a through-bore comprising, at the cylindrical head, an inner thread cooperating with a threaded profile of the straight cannula in order to immobilise the retaining element on said cannula.

The drilling device according to the present invention comprises a locking device of which the fixing nut comprises, in its inner portion, a first threaded bore which cooperates with that formed over the cylindrical portion of the sleeve of the retaining element, and a second inner bore coaxial with the first and having a conical inclination profile complementary to the outer profile of said sleeve.

The drilling device according to the present invention comprises an articulated drill bit comprising safety means ensuring recovery of the cutting end, should said articulated drill bit break.

The drilling device according to the present invention comprises an articulated drill bit of which the safety means are formed by a resilient thread or wire arranged inside the metal tube and, more specifically, between the protective sheath formed in one piece with the inner face of said tube and the outer face of the centering sheath in such a way that each end of said resilient thread cooperates with the grasping head of said centering sheath.

The drilling device according to the present invention comprises an articulated drill bit of which the safety means are formed by a resilient thread or wire arranged inside the metal tube and between the inner face thereof and the protective sheath in such a way that each end of said resilient thread cooperates with the grasping head of said centering sheath.

The drilling device according to the present invention comprises a resilient safety thread of which the ends respectively comprise a stop arranged in a seat of similar profile formed in the grasping head of the centering sheath.

BRIEF DESCRIPTION OF THE DRAWINGS

The invention itself, its features and the advantages it provides will be better understood upon reading the description below, given with reference to the accompanying exemplary and non-limiting drawings, in which:

FIGS. 2, 2a and 2b show the guide pin of the drilling device according to the present invention.

FIGS. 3, 3a and 3b show the pin grasper for placement of the guide pin of the drilling device according to the present invention.

FIGS. 4 and 4a to 4d show an articulated drill bit of the drilling device according to the present invention making it possible to drill a curved channel in the vertebral body of a spinal segment.

FIGS. 4e to 4j show a variant of the articulated drill bit of the drilling device according to the present invention, said drill bit comprising safety means ensuring recovery of the cutting end should the articulated drill bit break.

FIGS. 5a, 5b, 5d and 5e show a locking device making it possible to immobilise the articulated drill bit on the straight cannula of the drilling device according to the present invention.

DESCRIPTION OF THE PREFERRED EMBODIMENTS

Figure 1:
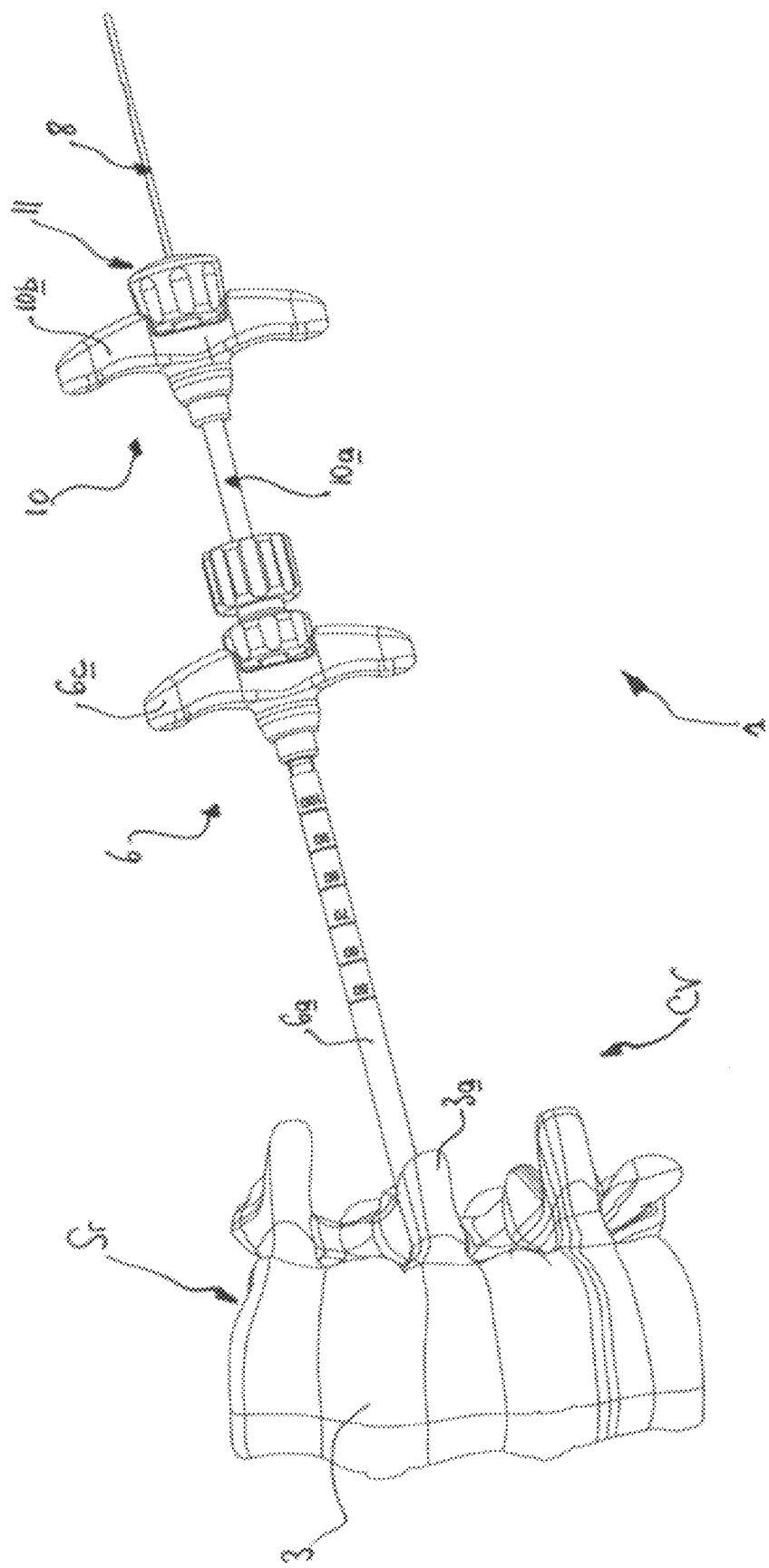
FIGS. 1 and 1a are perspective views illustrating the positioning of the cannula fixed in the vertebral body of a spinal segment for insertion of elements forming the drilling device according to the present invention.
Figure 1A:
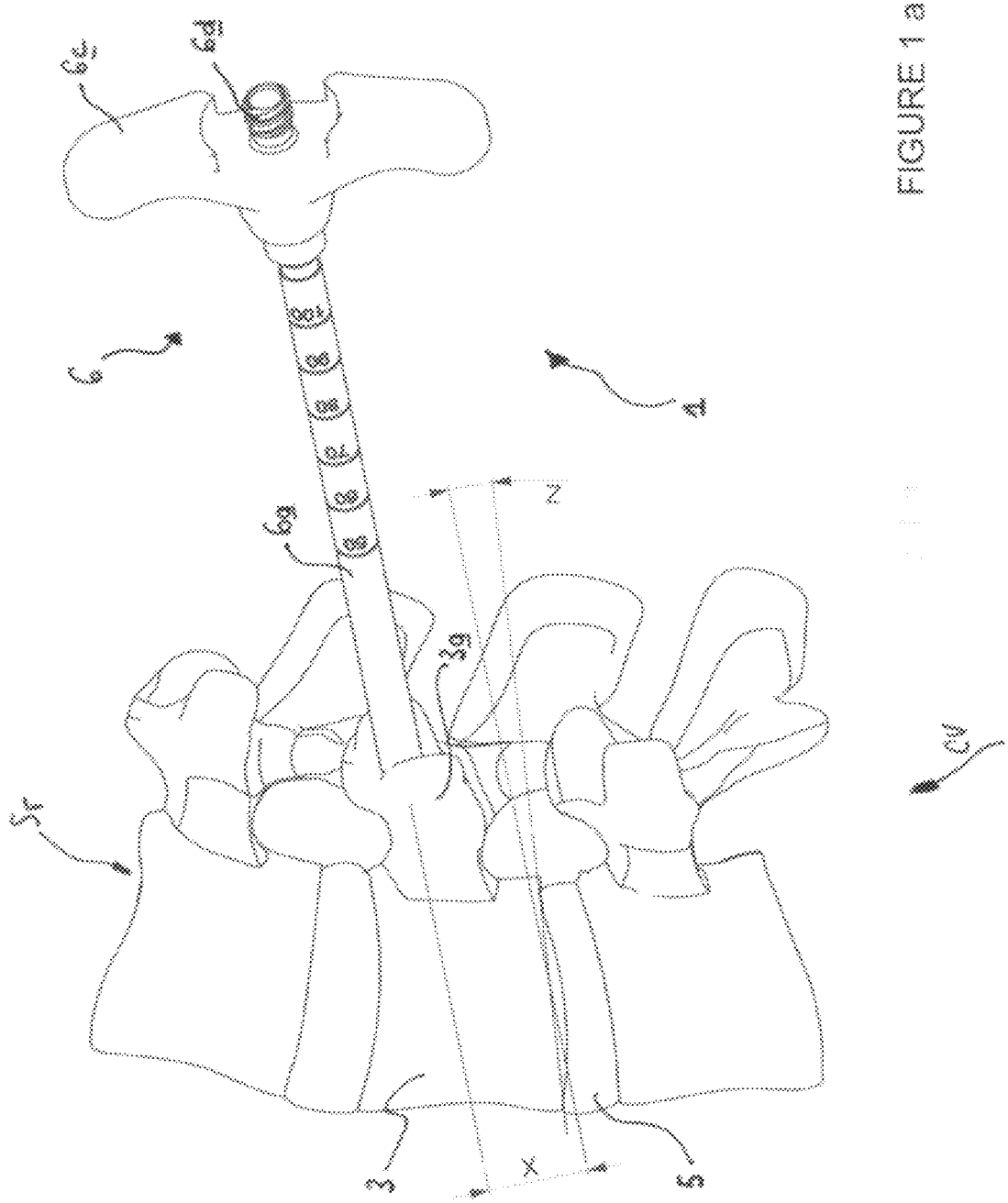
Figure 20:
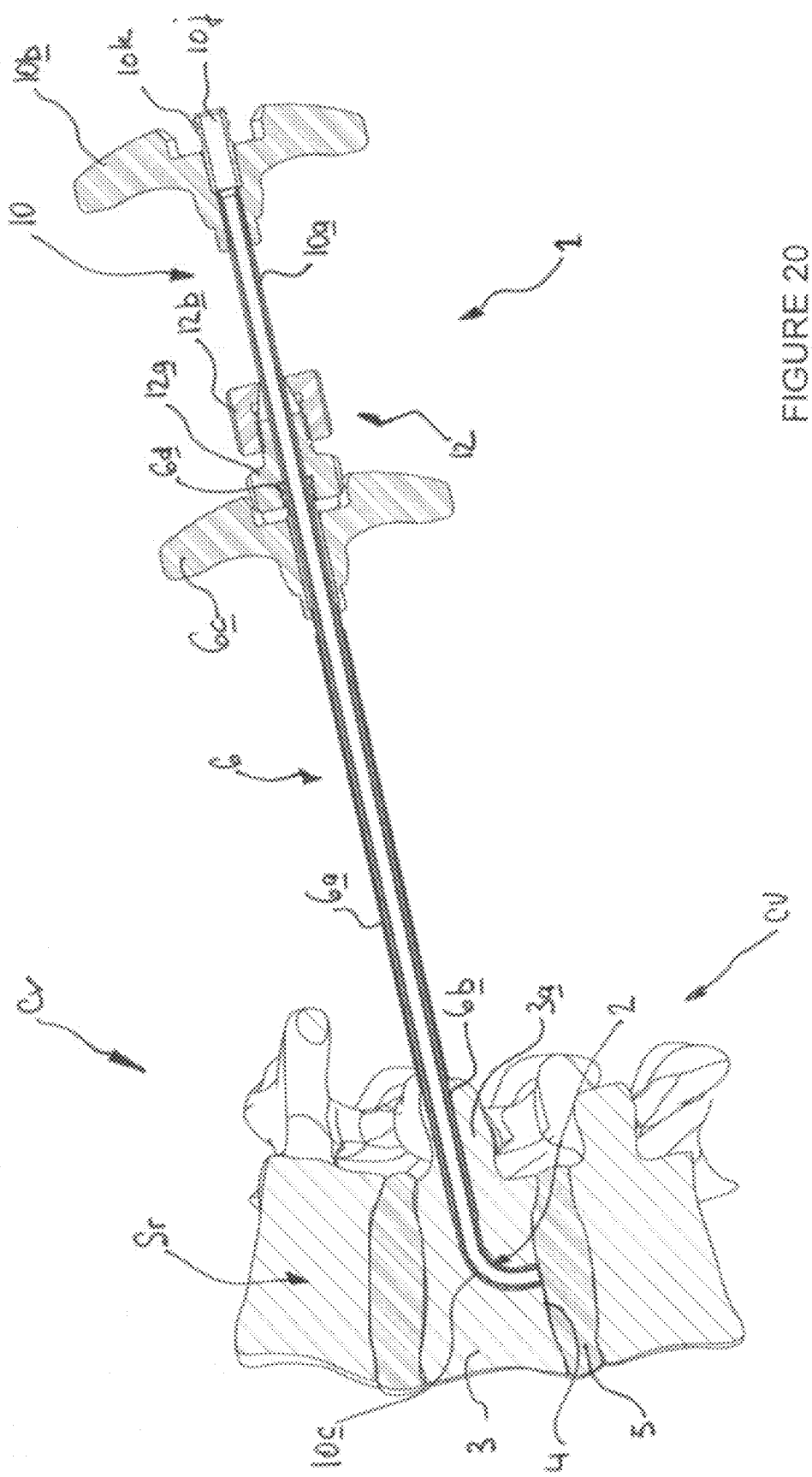

FIGS. 1, 1a and 20 show a drilling device 1 comprising an assembly of elements arranged so as to enable the formation of a curved osseous channel 2 inside the body of a vertebra 3 and the cortical plateau 4 of a spinal segment Sr of a vertebral column Cv in order to reach the upper face of a damaged intervertebral disc 5.

The drilling device 1 according to the present invention makes it possible to form a percutaneous, trans-osseous surgical approach in order to reach the nucleus of the intervertebral disc 5 in such a way that the necessary interventions can then be carried out on the damaged intervertebral disc.

The straight cannula 6 is screwed into the top of the pedicle 3a of the corresponding vertebra 3 in order to achieve the greatest distance x and the greatest angle z between said cannula and the lower plate of said vertebra (FIG. 1a).

Figure 13:
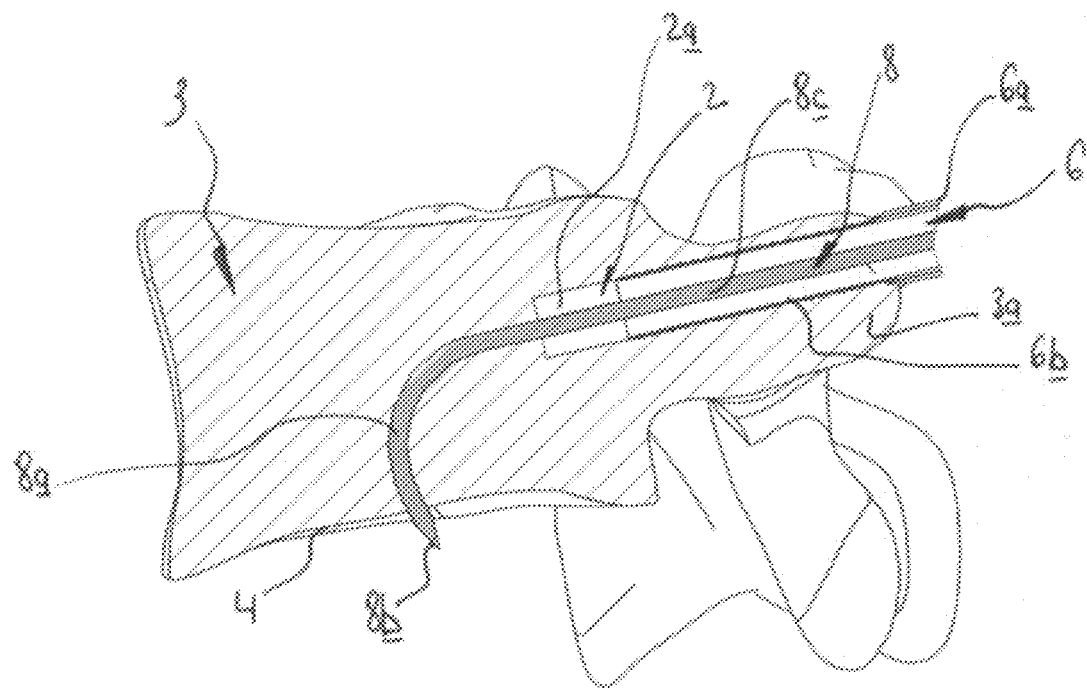

The straight cannula 6 is formed of a cylindrical tube 6a comprising, over its outer profile and at its free end, a thread 6b for its retention in the straight channel 2a formed previously (FIG. 13).

The cylindrical tube 6a is formed in one piece, at the end opposite that bearing the thread 6b, with a grasping grip 6c made of coloured plastics material. The cylindrical tube 6a extends beyond the grasping grip 6b with a threaded profile 6d, making it possible to fix other elements forming the drilling device 1 according to the present invention.

Figure 2:
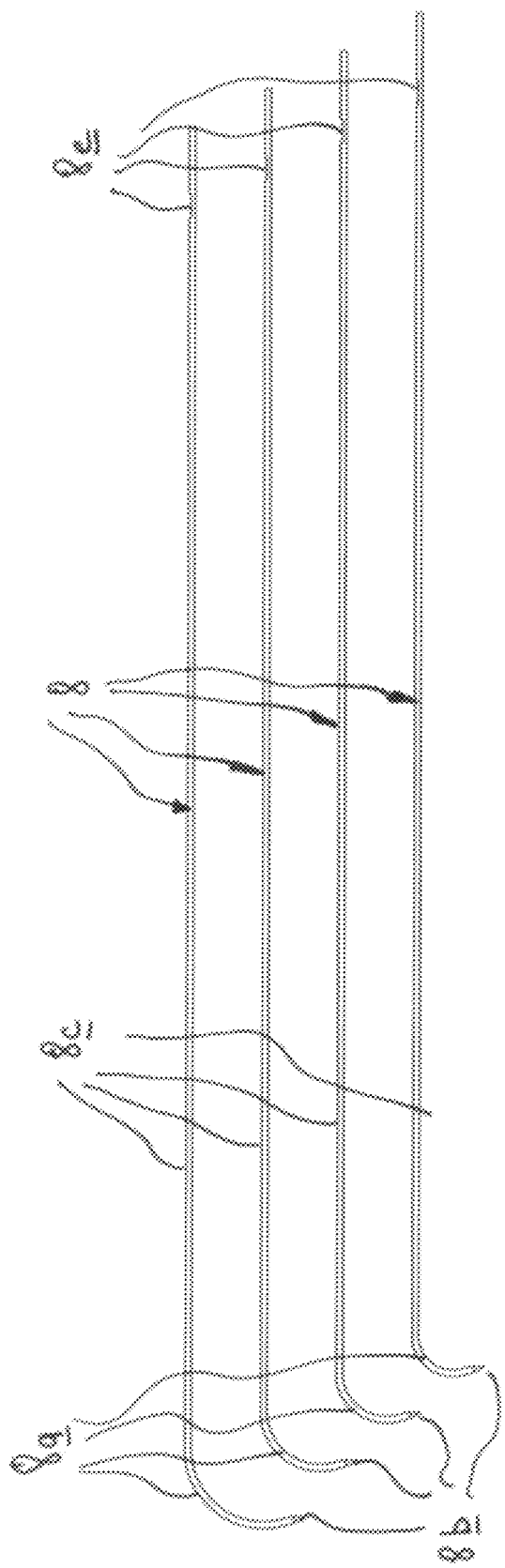
Figure 2:
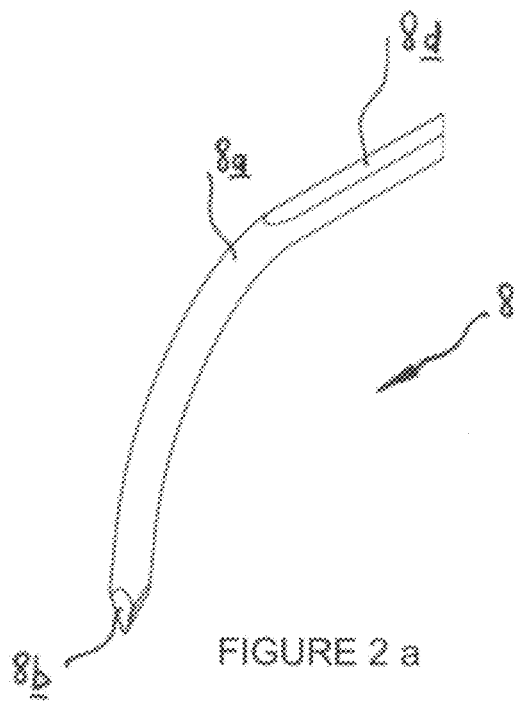
Figure 2:
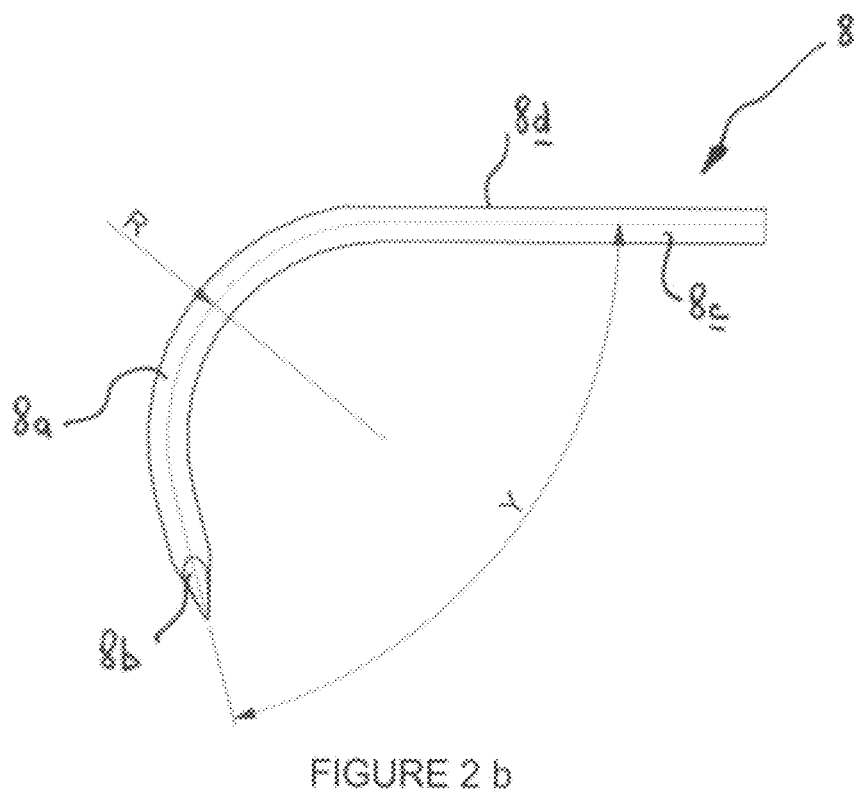

FIGS. 2, 2a and 2b show a kit of guide pins 8 making it possible to reach the center of the intervertebral disc 5 via the straight cannula 6 fixed previously in the body of the vertebra 3.

Each guide pin 8 is made of a material which is both hard-wearing and flexible, such as a Superelastic Nitinol alloy.

Each guide pin 8 has an outer diameter which is less than 3 millimeters and, at one of its ends, has a curved profile 8a of which the radius of curvature R is less than 20 millimeters.

In accordance with a preferred embodiment the guide pin 8 has an outer diameter which is between 10 millimeters and 20 millimeters and, at one of its ends, has a curved profile 8a of which the radius of curvature R is between 1.4 millimeters and 2 millimeters.

Each guide pin 8 comprises, at its curved end 8a, a sharpened tip 8b arranged in a direction defined by an angle Y which is less than 90 degrees to the longitudinal axis of said pin.

In accordance with a preferred embodiment each guide pin 8 comprises, at its curved end 8a, a sharpened tip 8b arranged in a direction defined by an angle Y which is between 70 and 85 degrees to the longitudinal axis of said pin.

Each guide pin 8 comprises a straight longitudinal portion 8c having a flattened part 8d which cooperates with a complementary profile 9a formed in a pin holder 9 (FIGS. 3 and 3a), making it possible to ensure on the one hand that the guide pin 8 is blocked against rotation inside the pin holder 9, and on the other hand that said guide pin 8 is rigidified over its straight longitudinal portion 8c during its insertion into the vertebral body 3 through the straight cannula 6 fixed previously.

Each guide pin 8 comprises, at its end opposite that with a curved profile 8a, a notch 8e formed in the straight longitudinal portion 8c and, more specifically, beside the flattened part 8d.

A guide pin 8 with a curved profile 8a with an adapted radius of curvature R is selected as a function of the distance X between the straight cannula 6 and the lower plateau of the corresponding vertebra 3.

Figure 3:
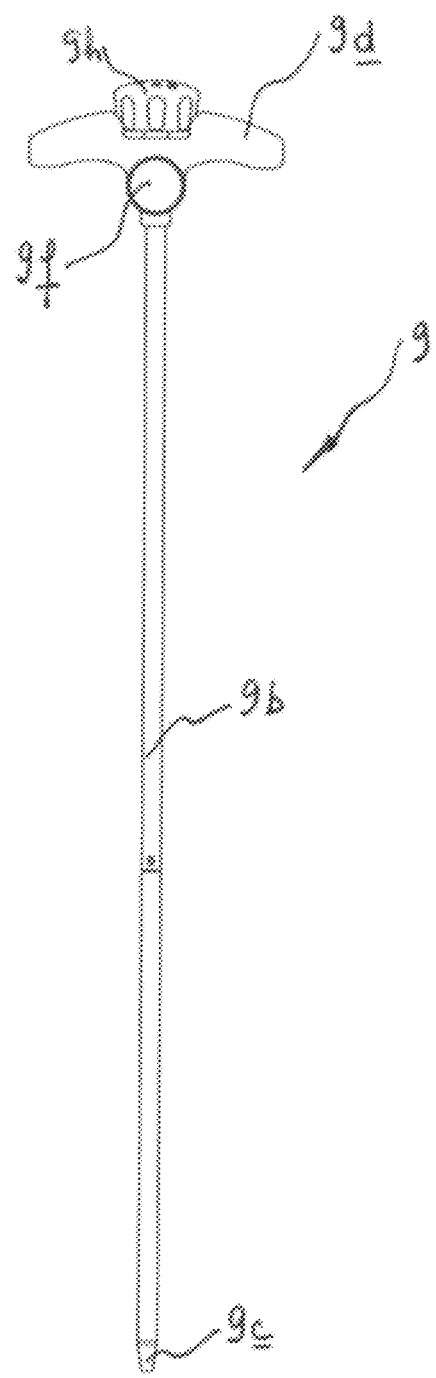

FIGS. 3, 3a and 3b show the pin holder 9 which is formed of a cylindrical metal tube 9b having a free end which is equipped on the one hand externally with a cone 9c enabling it to be slid inside the cannula 6, and on the other hand internally with the flattened part 9a with a profile complementary to that of the guide pin 8.

The combination of flattened parts between the pin holder 9 and the guide pin 8 makes it possible to orientate said guide pin 8 in the straight cannula 6 and to define an exit position of said guide pin which is constant and always identical.

The cylindrical tube 9b of the pin holder 9 is formed in one piece, opposite its free end, with a grasping grip 9d made of coloured plastics material and equipped with a tensioning screw 9e.

The tensioning screw 9e is provided to pass through the cylindrical tube 9b and emerge inside the notch 8e formed in the guide pin 8 so as to block said guide pin against movement in translation and against rotation inside said pin holder 9.

The grasping grip 9d comprises, in the extension of the cylindrical tube 9b, a hollow cylindrical sleeve 9f penetrated by the guide pin 8. The cylindrical sleeve 9f has, over its outer profile, a fast thread 9g making it possible to screw on a plug 9h made of coloured plastics material.

Once screwed onto the grasping grip 9d, the plug 9h abuts the guide pin, making it possible to temporarily block said guide pin 8 against movement in translation relative to the pin holder 9 (FIG. 3b).

FIGS. 4, 4a to 4d and 18 show an articulated drill bit 10 of the drilling device 1 according to the present invention, which articulated drill bit is intended to extend the previously formed straight osseous channel 2a by a curved channel 2b ending above the intervertebral disc 5.

The articulated drill bit 10 is formed of a metal cylindrical tube 10a comprising, at one of its ends, a grasping grip 10b made of coloured plastics material, whereas the other end is cropped in accordance with a profile 10c which may be formed, for example, of a sequence of alternately concave and convex loops 10d ensuring deformation and articulation of said end in a curved shape.

The metal tube 10a terminates after the profile 10c via a cutting end 10m comprising a first set of teeth 10e arranged over the periphery of said tube and of which the cutting edge 10f of each tooth is slightly inclined relative to the longitudinal axis of the articulated drill bit 10.

The cutting end 10m comprises a second set of teeth 10g which is arranged at the end of the metal tube 10a and of which each cutting edge 10h is sharply inclined so as to intersect the longitudinal axis of the articulated drill bit 10.

The articulated drill bit 10 comprises, in the inner portion of the metal tube 10a, a protective sheath 10i made of a resilient material making it possible to internally smooth the irregularities and gaps in the free end arising from the profile 10c formed, for example, by the sequence of alternately concave and convex loops 10d.

The protective sheath 10i may be made, for example, of a resilient material such as PTFE, also ensuring a significant coefficient of slip enabling sliding either of the guide pin 8 or of a centering sheath 11 during drilling of the curved channel 2b (FIG. 4c).

Figure 4:
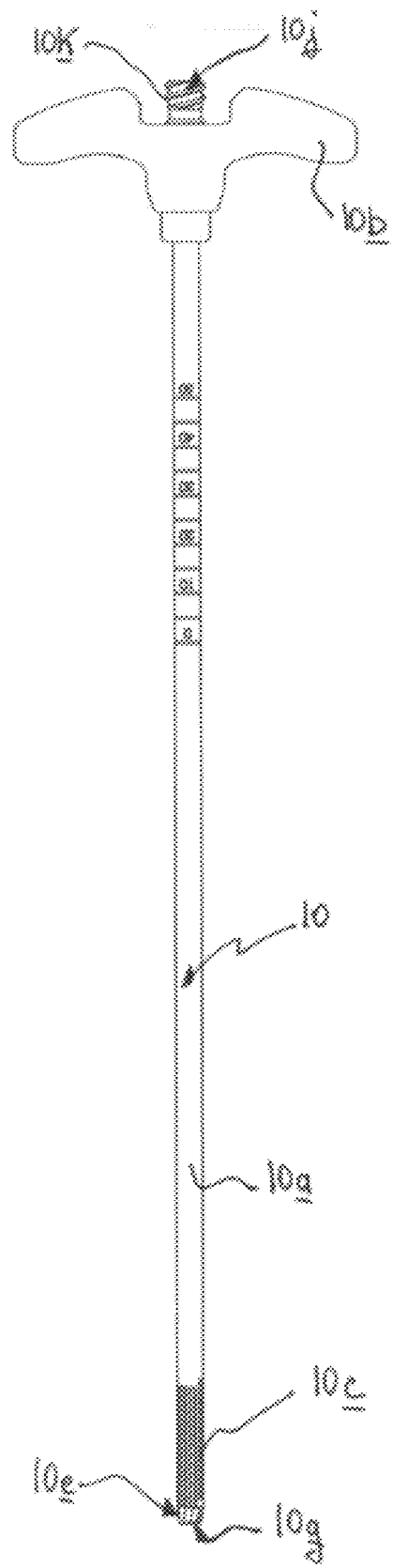
Figure 4:
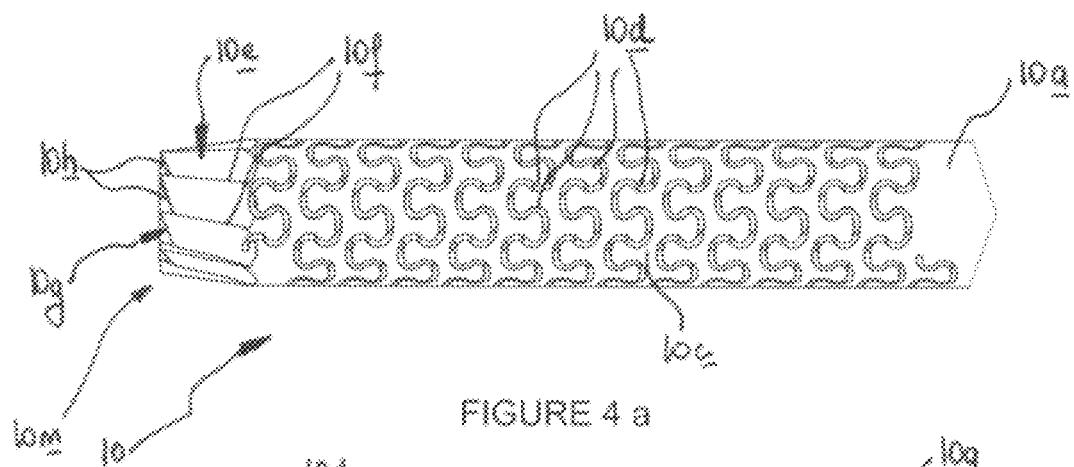
Figure 4:
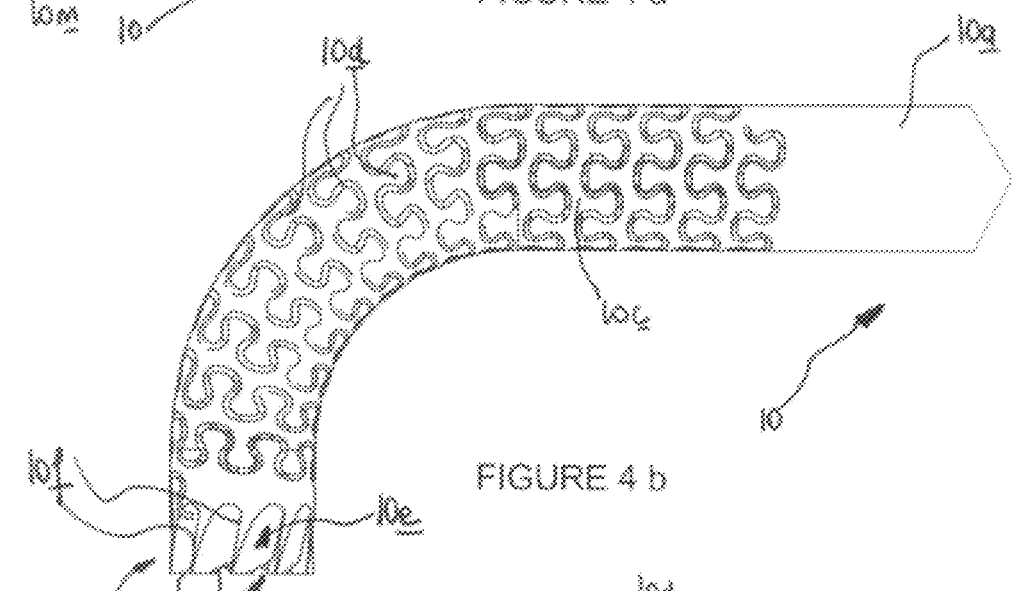
Figure 4:
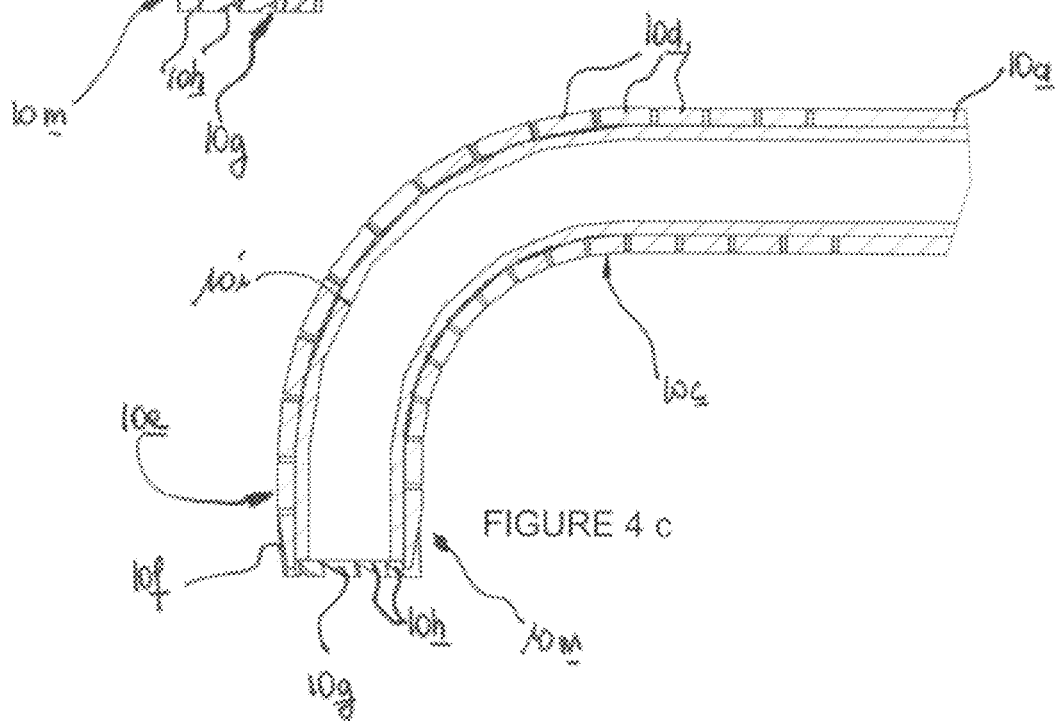
Figure 4:
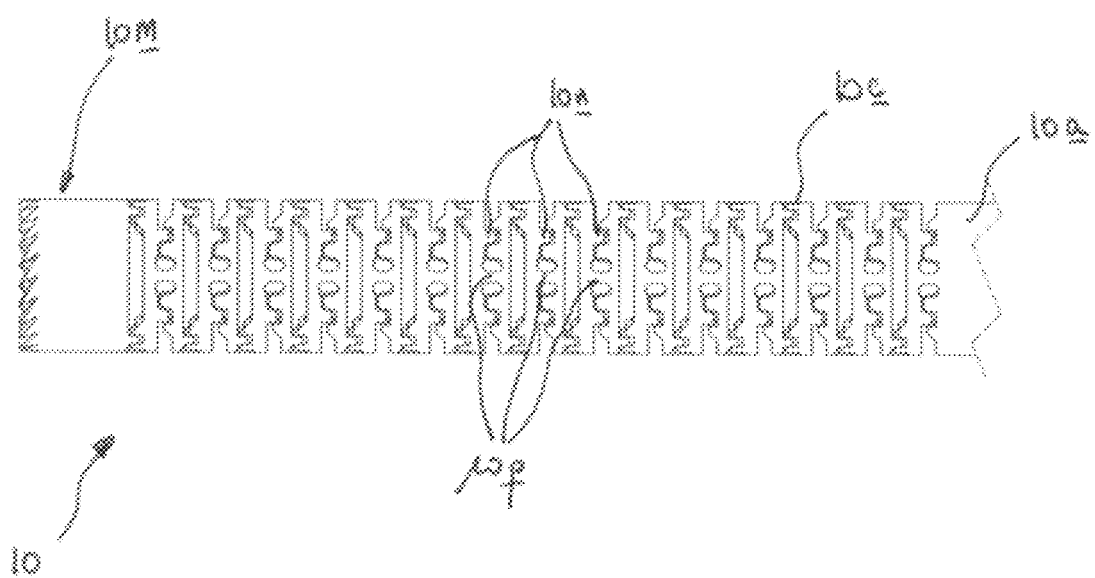
Figure 4E:
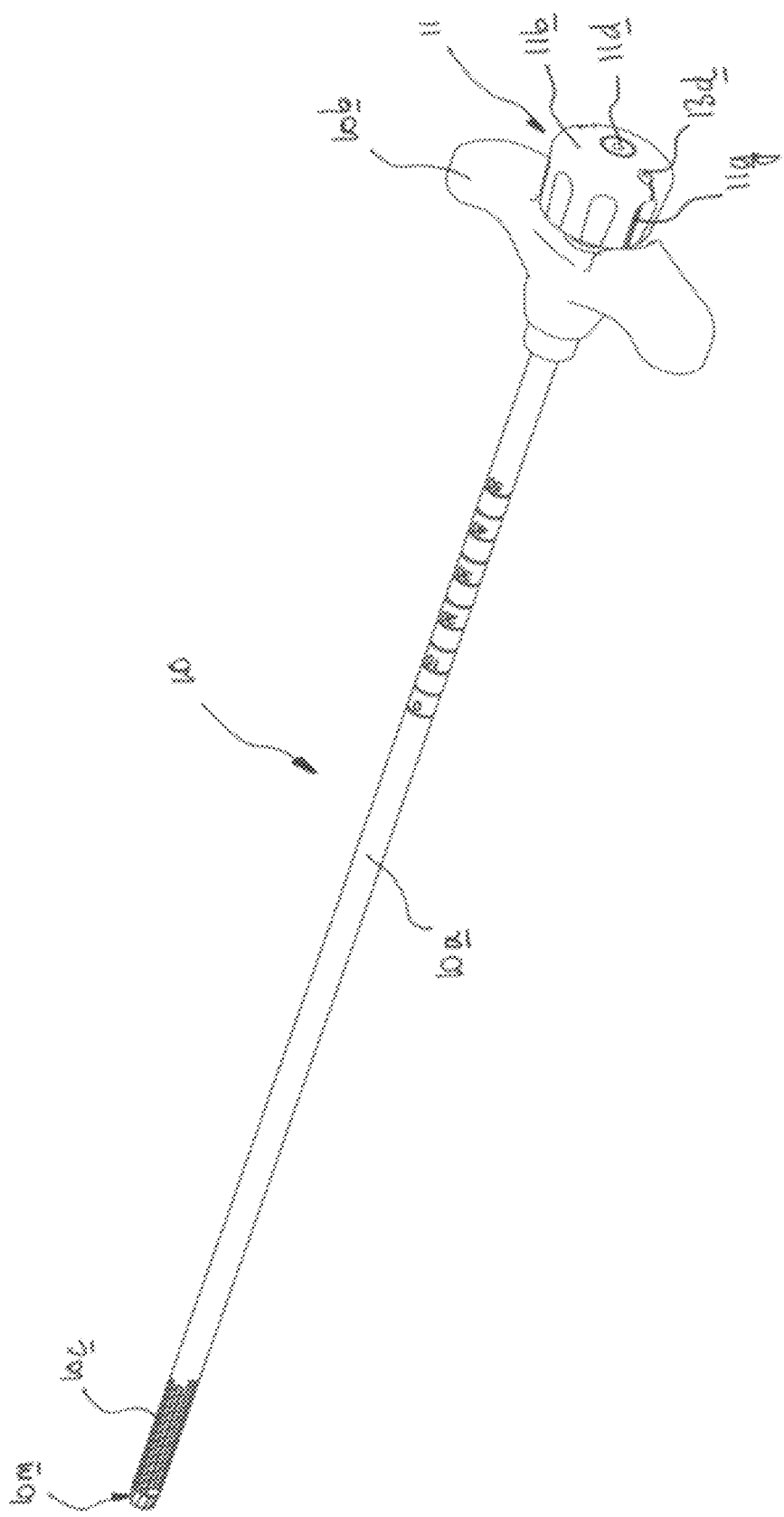
Figure 4:
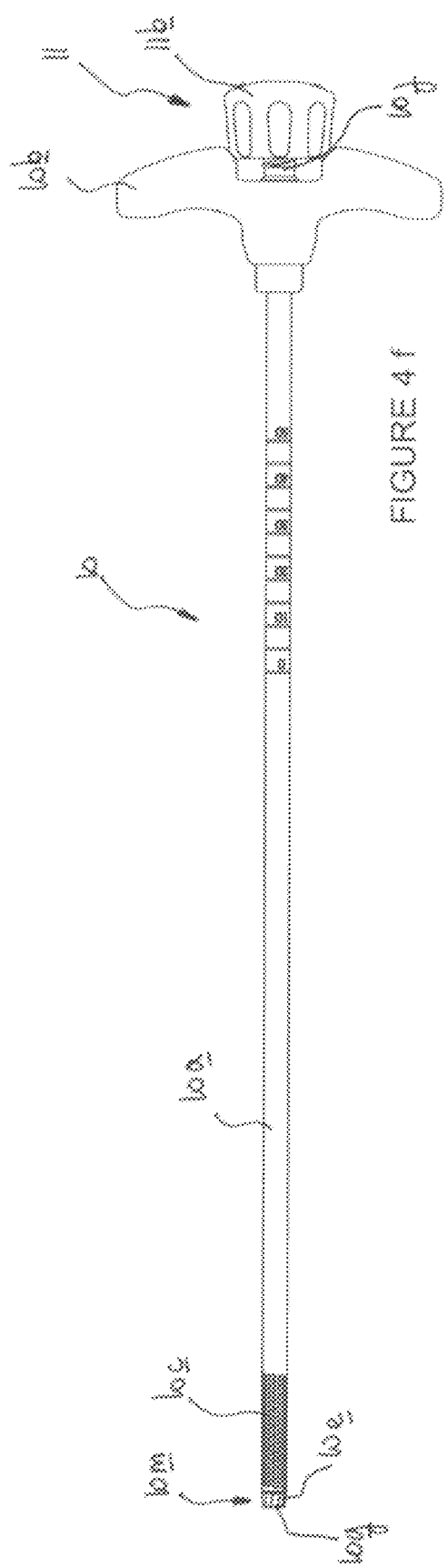
Figure 4:
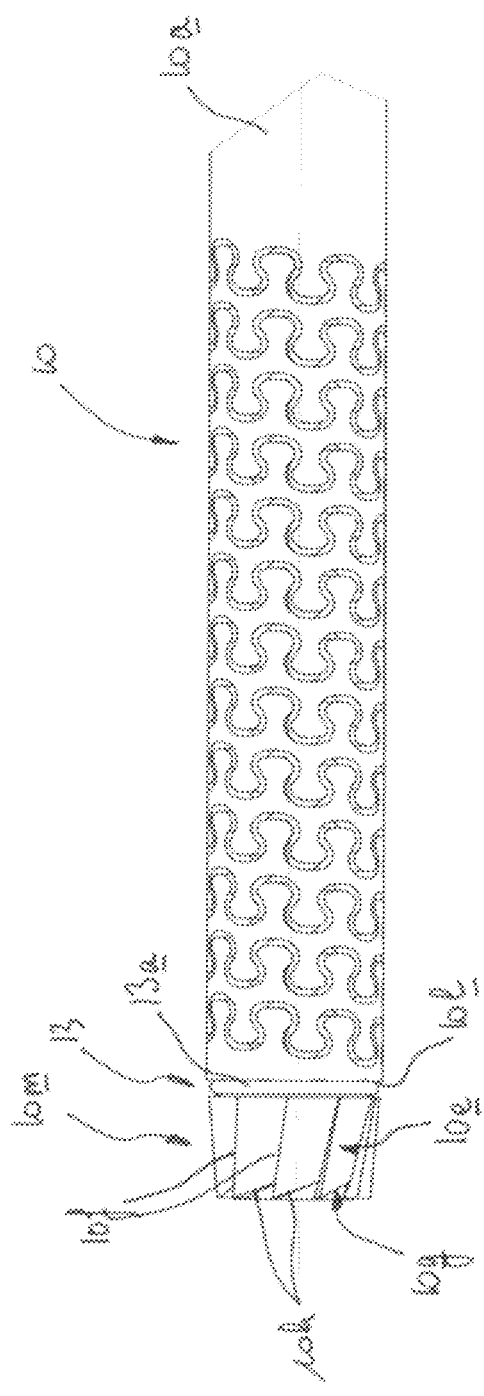
Figure 4:
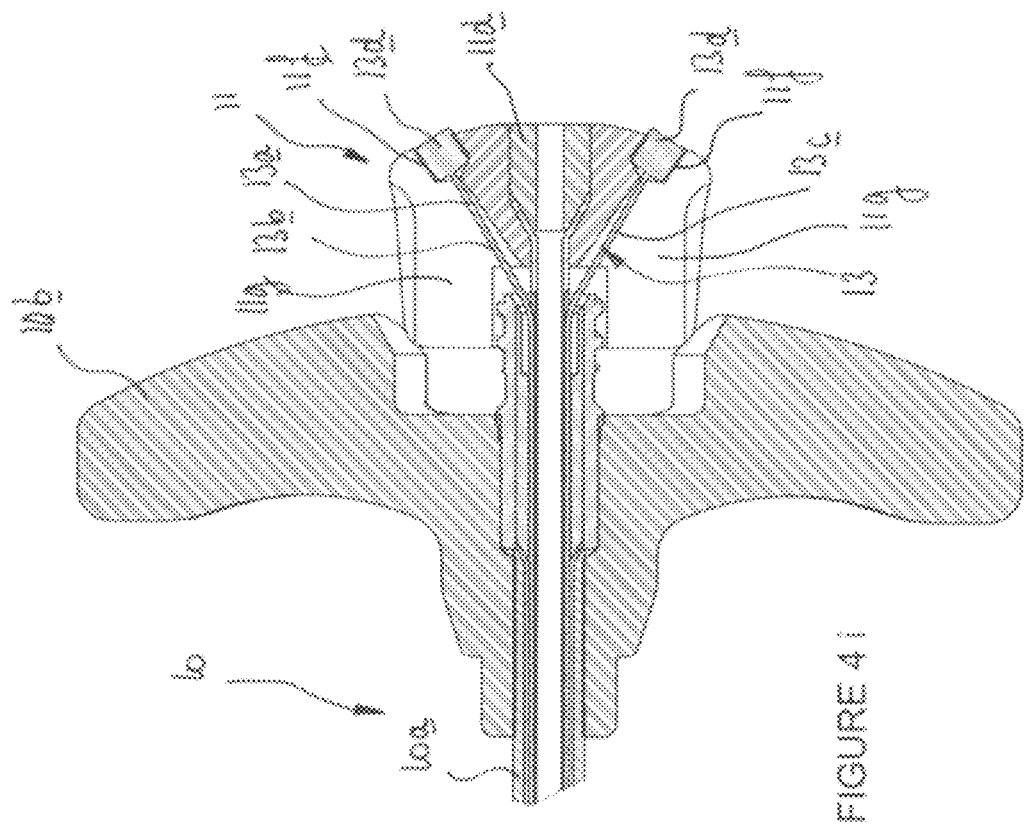
Figure 4:
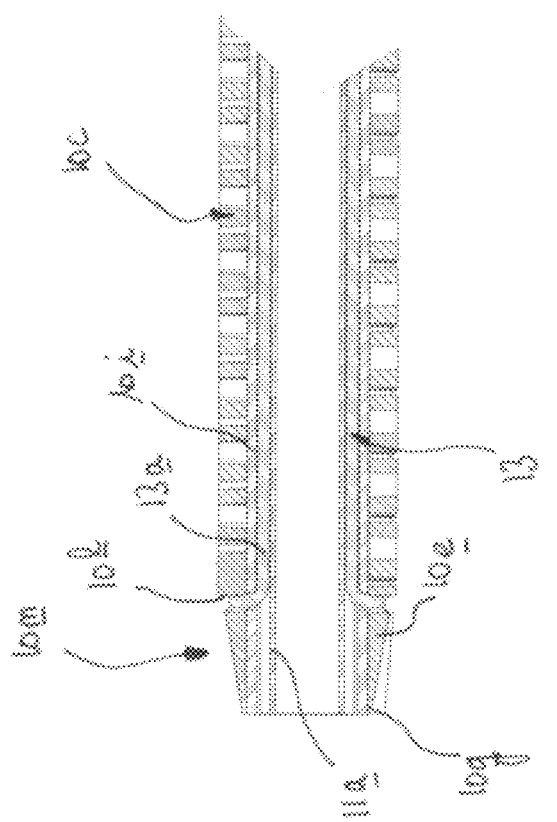
Figure 4J:
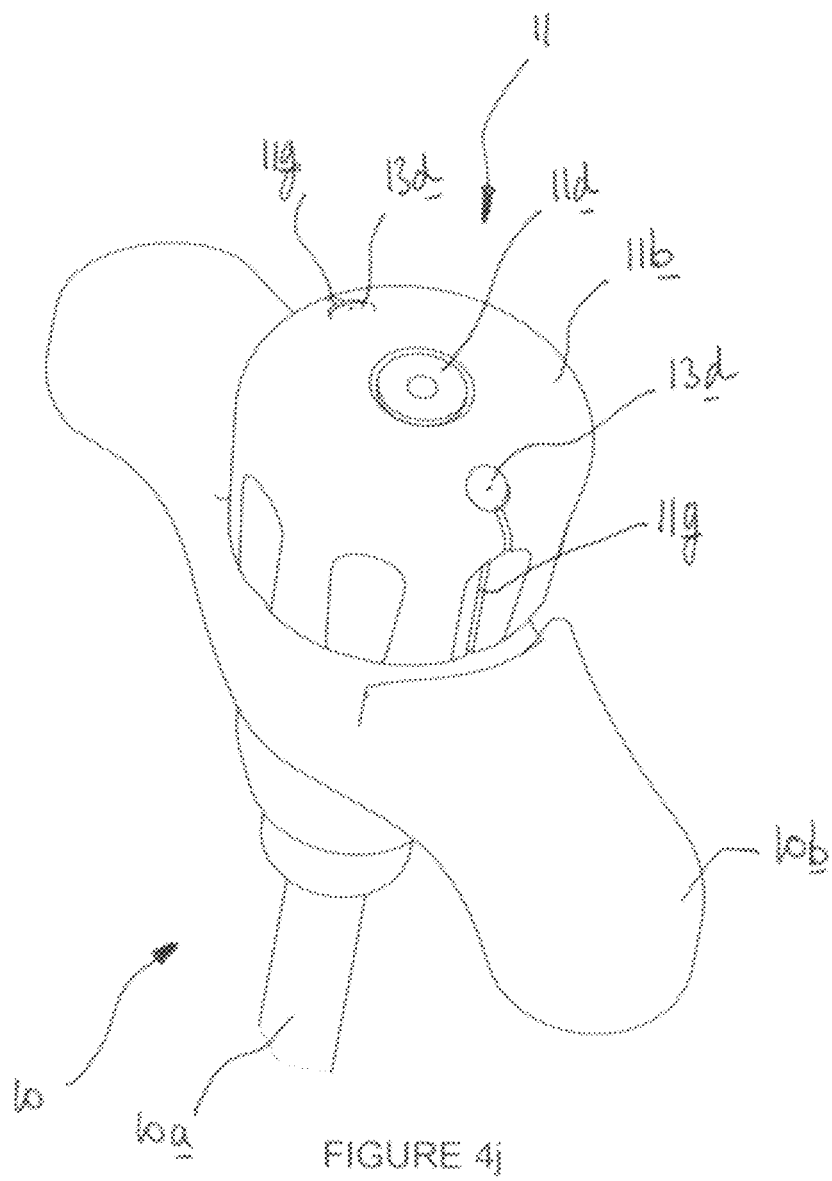
Figures 5, 5C:
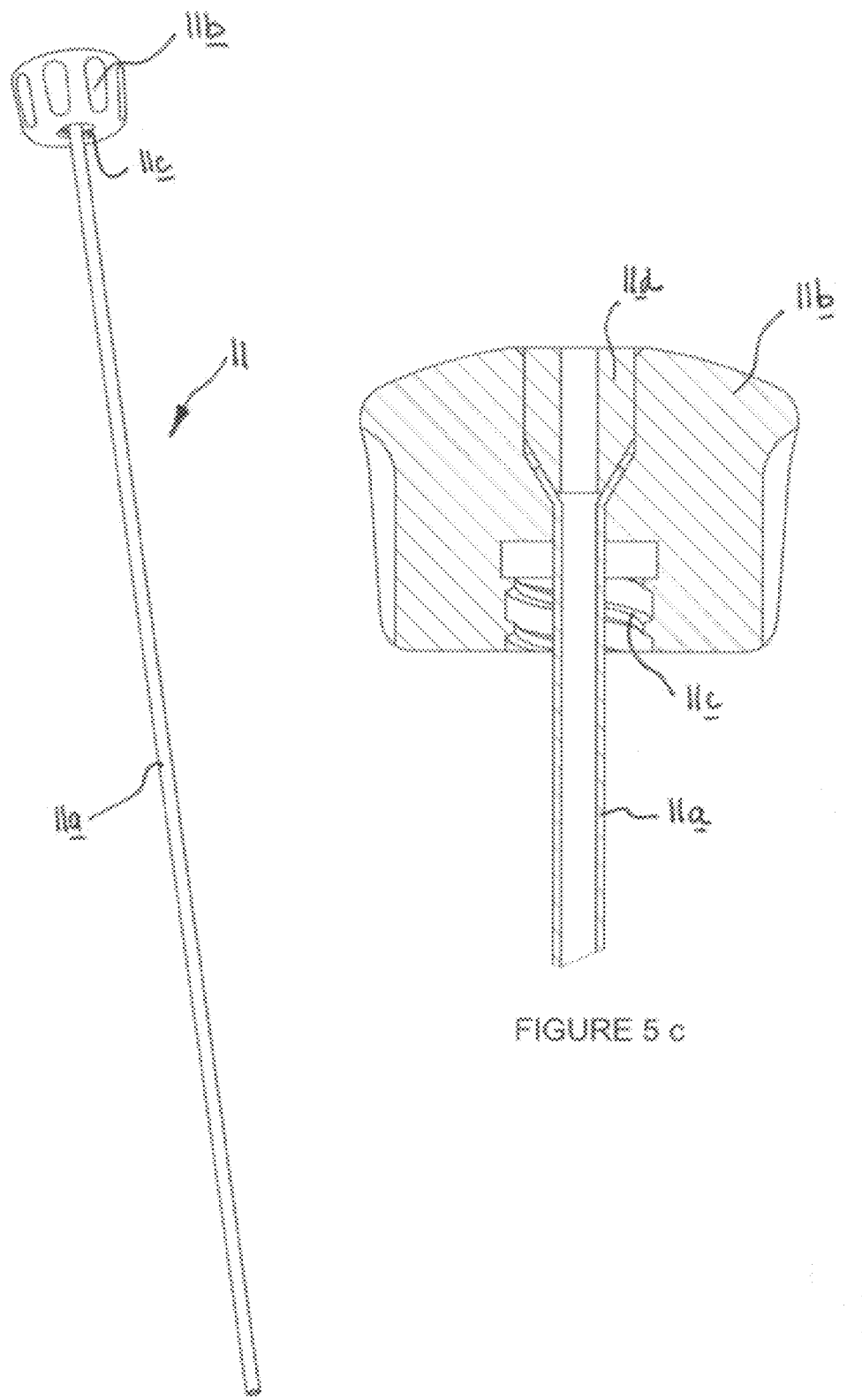
FIGS. 5 and 5c show a centering sheath for placement of the articulated drill bit around the guide pin and in the cannula of the drilling device according to the present invention.
Figure 5A:
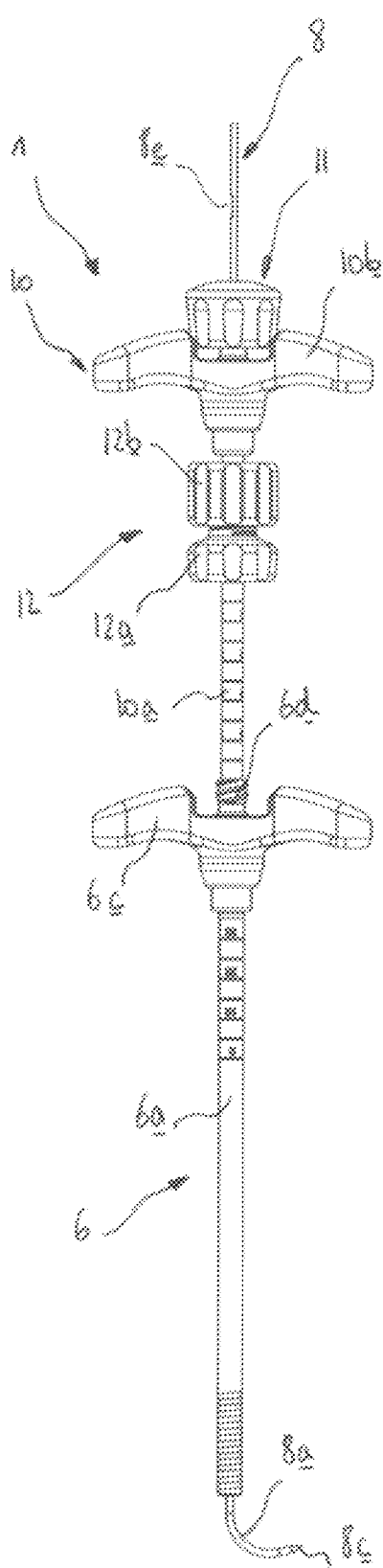
Figure 5B:
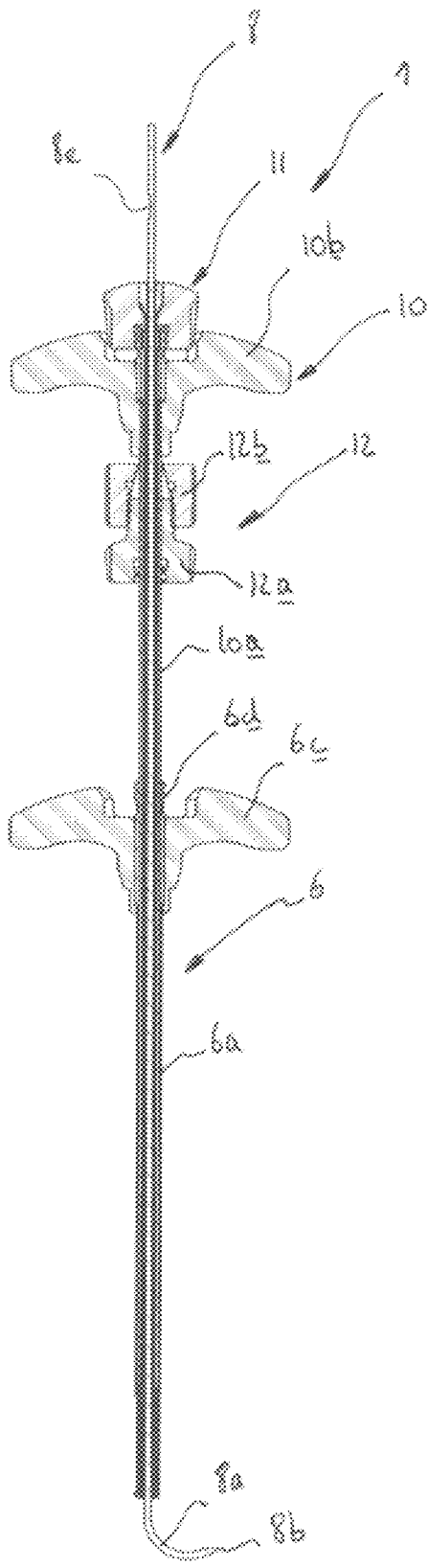

The grasping grip 10b comprises, in the extension of the cylindrical tube 10a, a hollow cylindrical sleeve 10j having, over its outer profile, a fast thread 10k making it possible to screw in a centering sheath 11 (FIGS. 4 and 5).

FIG. 4d shows a variant of the profile 10c provided at the free end of the metal tube 10a of the articulated drill bit 10. The profile 10c is obtained by a Cardan-type cut comprising stops 10n between each connection point 10p. The stops 10n make it possible to form a block preventing the profile 10c from deforming too significantly during its deformation in a curved shape.

FIGS. 4e to 4j show a variant of the articulated drill bit 10 which may comprise safety means 13 ensuring recovery of the cutting end 10m should said articulated drill bit break.

The safety means 13 are formed of a resilient thread or wire 13a arranged inside the metal tube 10a and, in accordance with a first embodiment, said resilient thread or wire 13a can be placed between the protective sheath 10i, which is formed in one piece with the inner face of said tube, and the outer face of the centering sheath 11.

In accordance with a second embodiment the resilient thread or wire 13a can be arranged between the inner face of the metal tube and the protective sheath 10i.

The resilient safety thread 13a ends outside the metal tube 10a, on the hand at the cylindrical sleeve 10j so each end 13b, 13c of said resilient thread 13a cooperates with the grasping head 11b of the centering sheath 11, and on the other hand in a peripheral gap 10l formed between the cutting end 10m and the profile 10c, ensuring the deformation of said drill bit 10.

The resilient safety thread 13a is passed through two small holes formed in the protective sheath 10i and the metal tube 10a so as to emerge inside the peripheral gap 10l so said resilient thread forms a safety loop between the cutting end 10m and the profile 10c, which ensures the deformation of said drill bit 10, whereas the resilient thread 13a emerges in two strands, of which each of the ends 13b, 13c is housed in the grasping head 11b of the centering sheath 11.

The ends 13b, 13c of the resilient safety thread 13a respectively comprise a stop 13d arranged in a seat 11f of similar profile formed in the grasping head 11b. Said grasping head comprises slots 11g which are diametrically opposed and open into each seat 11f to allow placement of the two resilient safety threads 13a.

The flexible safety thread 13a connects the cutting end 10m of the articulated drill bit 10 to the exterior thereof so as to make it possible, should said drill bit break, to fully extract said drill bit without leaving behind any debris inside the vertebral body 3.

Similarly, when the curved channel 2b is drilled without any breakage of the articulated drill bit 10, the resilient safety thread 13a is extracted from said drill bit once at least one of the stops 13d has been removed and by simply pulling on one of the strands of said resilient thread.

FIG. 5 shows the centering sheath 11 which is formed of a cylindrical tube 11a made of a resilient material such as PTFE and is formed in one piece at one of its ends with a grasping head 11b made of coloured plastics material.

The grasping head 11b has, near the cylindrical tube 11a, a threaded inner bore 11c for cooperation with the sleeve 10j of the grip 10b of the articulated drill bit 10 for immobilisation thereof (FIG. 5c).

Similarly, the grasping head 11b comprises, opposite the threaded inner bore 11c, a blocking device 11d making it possible, by pinching, to block the movement in translation of the cylindrical tube 11a inside said head of the centering sheath 11 (FIG. 5c).

The centering sheath 11 makes it possible on the one hand to close the working clearance between the guide pin 8 and the articulated drill bit 10, and on the other to distance the teeth 10g with a cutting edge 10h from the articulated drill bit 10 of the guide pin 8 during drilling of the curved channel 2b.

FIGS. 5a, 5b, 5d and 5e show a locking device 12 arranged on the metal tube 10a and beneath the grasping grip 10b of the articulated drill bit 10 of the drilling device 1.

The locking device 12 can slide freely over the metal tube 10a in order to be screwed onto the threaded profile 6d of the straight cannula 6 when the articulated drill bit 10 is correctly positioned so as to avoid any displacement thereof after drilling of the curved channel 2b.

The locking device 12 is formed of a retaining element 12a and of a fixing nut 12b making it possible to rigidly fix the assembly on the metal tube 10a of the articulated drill bit 10. The retaining element 12a comprises a cylindrical head 12c formed in one piece with a sleeve 12d having a cylindrical outer profile 12e provided with a thread 12f extending via a split, conical outer profile 12g.

The retaining element 12a is perforated through its middle by a through-bore 12h comprising, at the cylindrical head 12c, an inner thread 12i cooperating with the threaded profile 6d of the straight cannula 6 for immobilisation of said retaining element on said cannula.

The fixing nut 12b comprises, in its inner portion, a first threaded bore 12j which cooperates with that 12f formed in the cylindrical portion 12e of the sleeve 12d of the retaining element 12a, and a second inner bore 12k which is coaxial with the first and has a conical inclination profile complementary to the outer profile 12g of said sleeve 12d.

The locking device 12 is previously assembled around the metal tube 10a of the articulated drill bit 10, that is to say the fixing nut 12b is screwed onto the retaining element 12a without exerting any lock-up pressure on the inner through-bore 12h which is in contact with the outer periphery of said metal tube 10a.

In fact, the lock-up pressure is caused by complete screwing of the fixing nut 12b on the retaining element 12a in such a way that the conical bore 12k rests against the outer conical profile 12g of the sleeve 12d, making it possible to deform the inner bore 12h and therefore to create lock-up pressure over the outer periphery of the metal tube 10a.

FIGS. 6 to 13 show the different steps making it possible to position a guide pin 8 provided from the kit, of which the features relating to the radius of curvature R and the angle Y of the sharpened tip 8b have been previously determined as a function of the dimensions of the vertebra 3 to be drilled and the position of the intervertebral disc 5.

For this, the straight cannula 6 is previously fixed in the channel 2a formed at the top of the pedicle 3a and in the direction of the center of the vertebra 3 of the spinal segment Sr.

Figure 6:
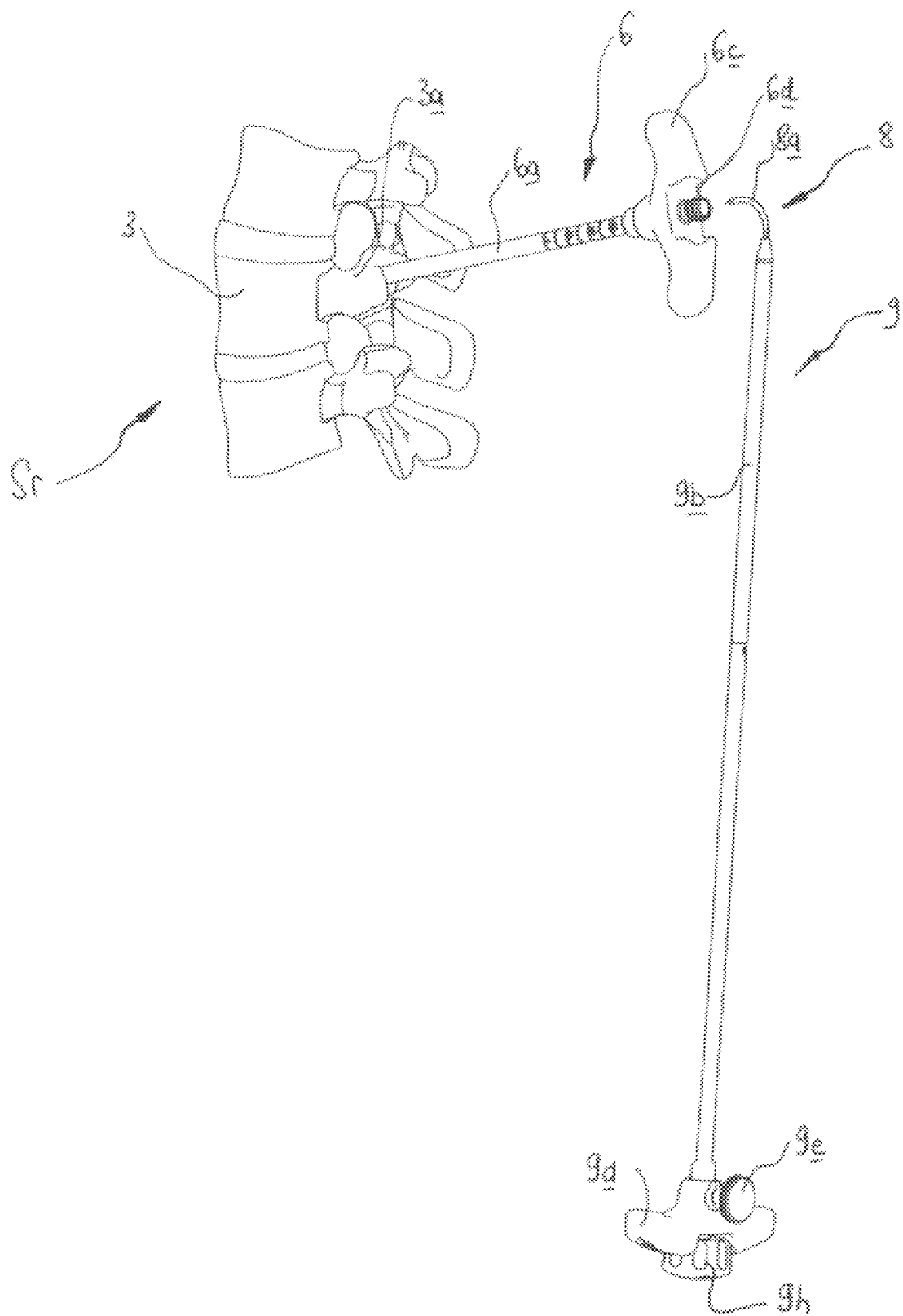
FIGS. 6 to 13 show the different steps making it possible to place the guide pin inside the vertebral body of a vertebra using the drilling device according to the present invention.

The corresponding guide pin 8 is inserted into the pin holder 9 and immobilised in translation and rotation relative to said pin holder via the tensioning screw 9e and the plug 9h (FIG. 6).

Figure 7:
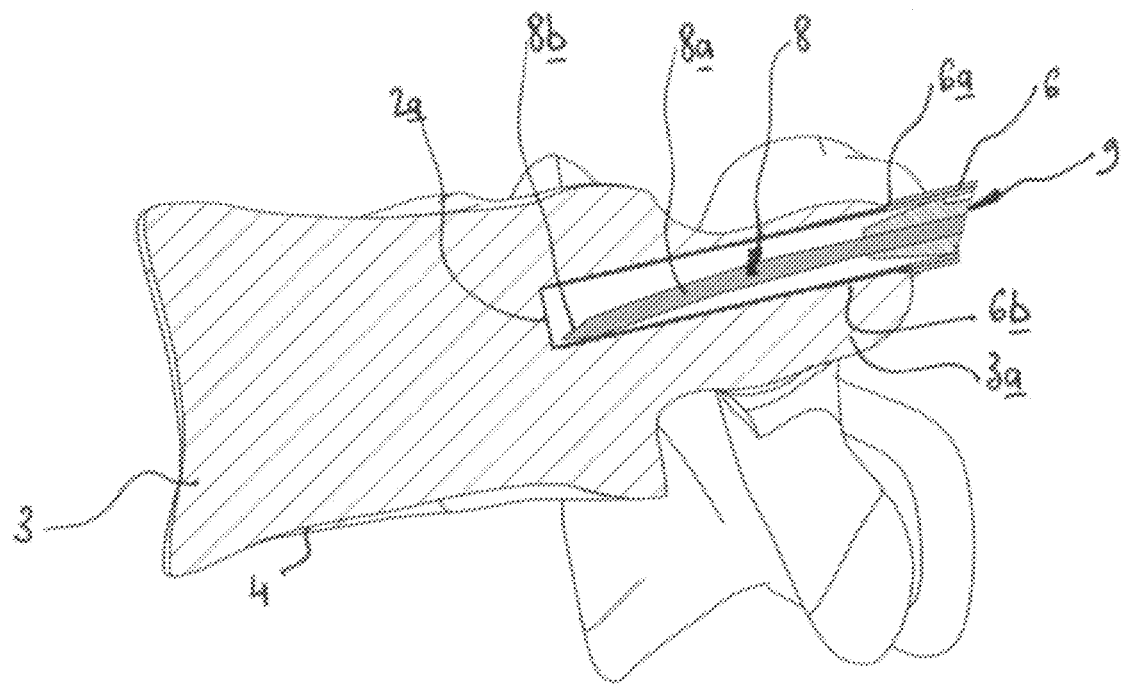

The pin holder 9 equipped with the guide pin 8 is inserted inside the straight cannula 6 until the curved end 8a of said guide pin is inside the straight channel 2a. The curved end 8a is constrained inside the tube 6a of the straight cannula 6 owing to the resilient nature of the guide pin 8 (FIG. 7).

The pin holder 9 is displaced in translation inside the tube 6a of the straight cannula 6 until the free end with a conical profile 9c penetrates the spongy bone of the body of the vertebra 3 (FIGS. 8 to 11).

The displacement of the pin holder 9 inside the tube 6a of the straight cannula 6 makes it possible to guide the sharpened end 8b of the guide pin 8 outside said tube 6a so said guide pin penetrates inside the spongy bone of the vertebra 3.

Figure 8:
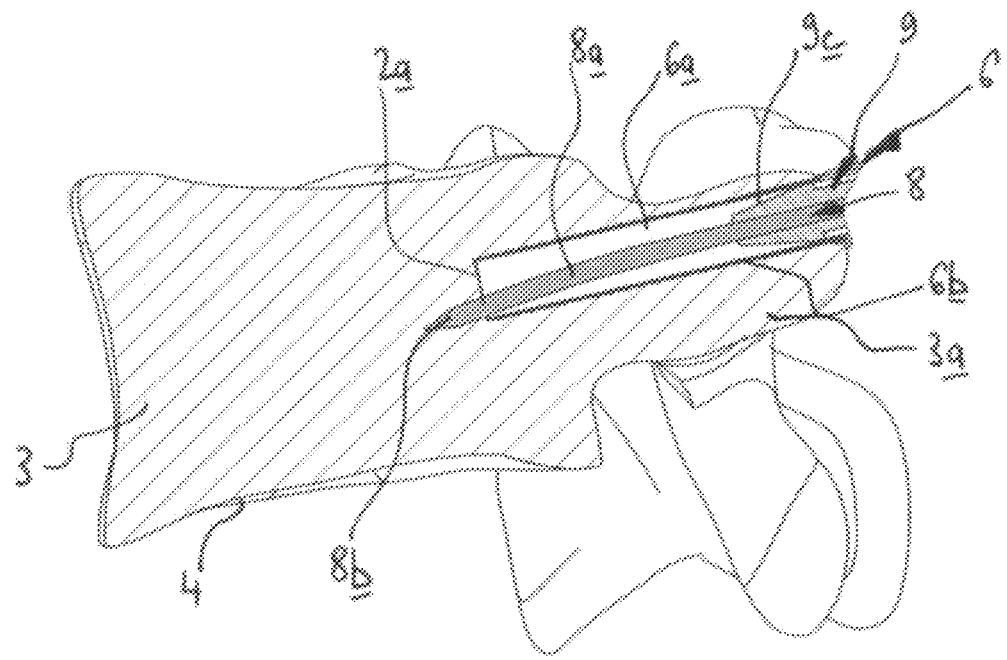
Figure 9:
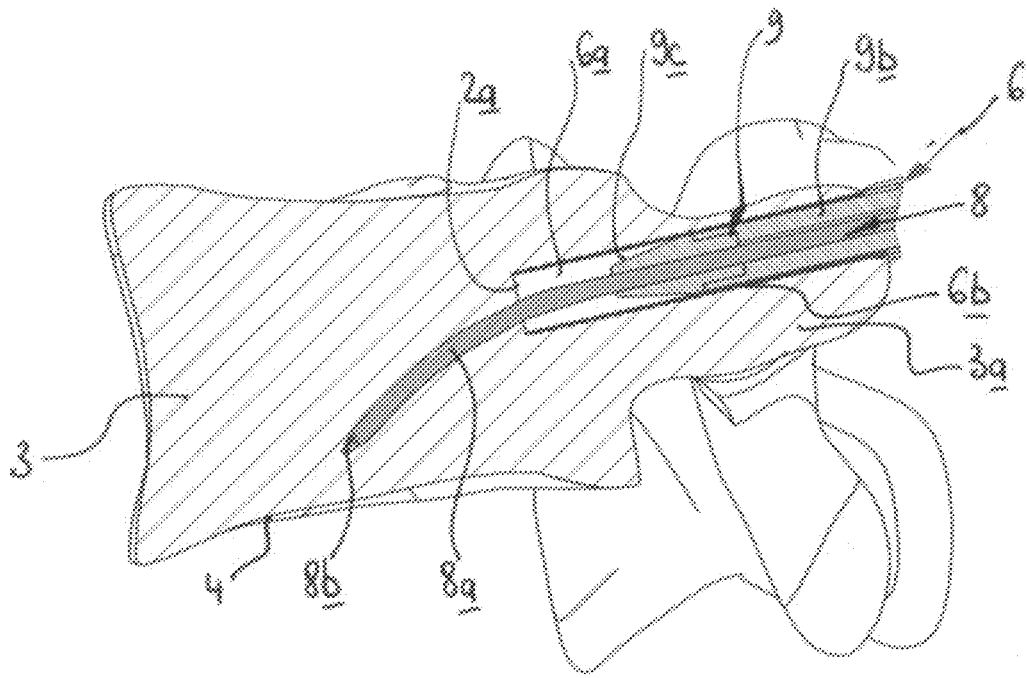
Figure 10:
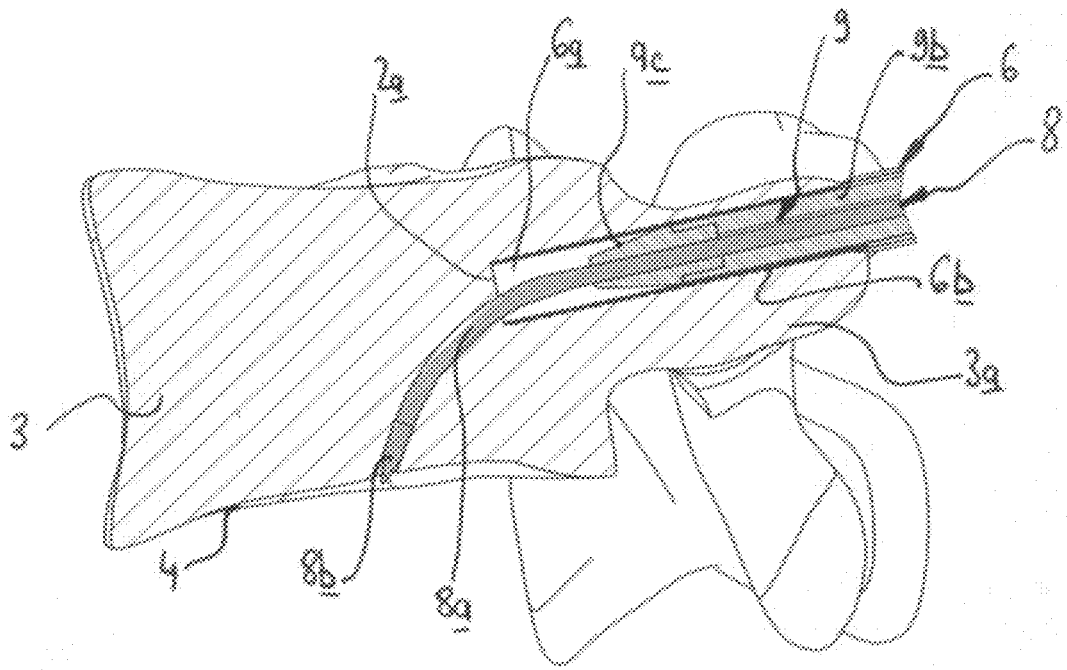

Owing to its resilient nature, the curved profile 8a of the guide pin 8 progressively resumes its radius of curvature R during the advancement of the pin holder 9 in the tube 6a. The sharpened tip 8b of the guide pin is thus directed progressively toward the cortical plate 4 of the vertebra 3 in order to be placed just above the intervertebral disc 5 (FIGS. 8 to 10).

Figure 11:
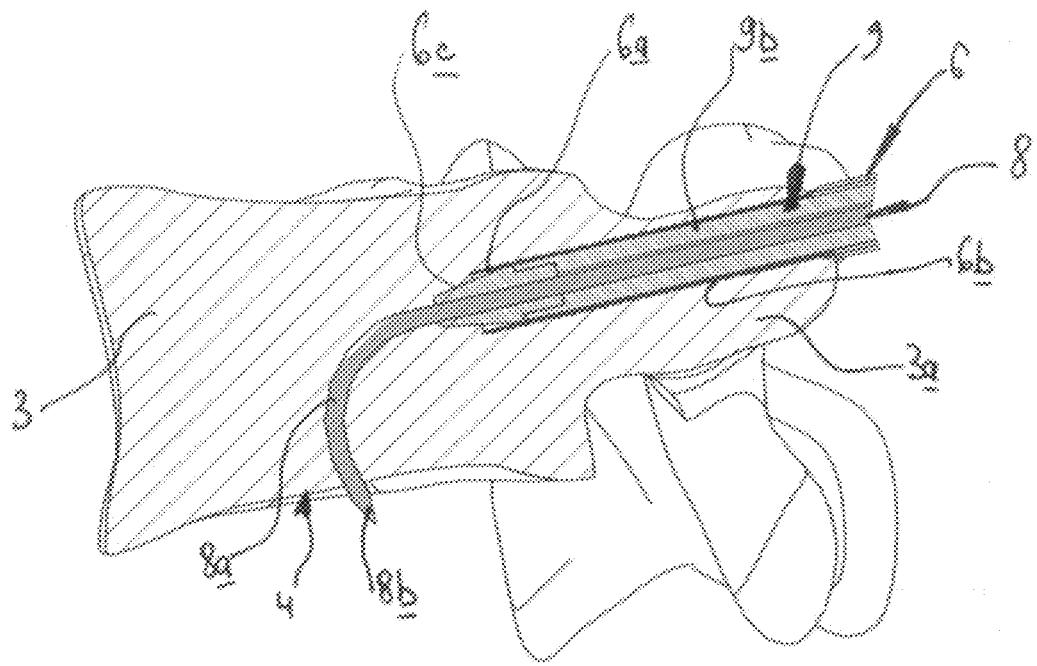

The pin holder 9 is displaced in translation in such a way that its free end with a conical profile 9c penetrates the spongy bone of the vertebra 3, making it possible for the guide pin 8 and, more specifically, its curved profile 8a to resume its initial radius of curvature R whilst passing through the cortical plateau 4 toward the intervertebral disc 5 (FIG. 11).

Figure 12:
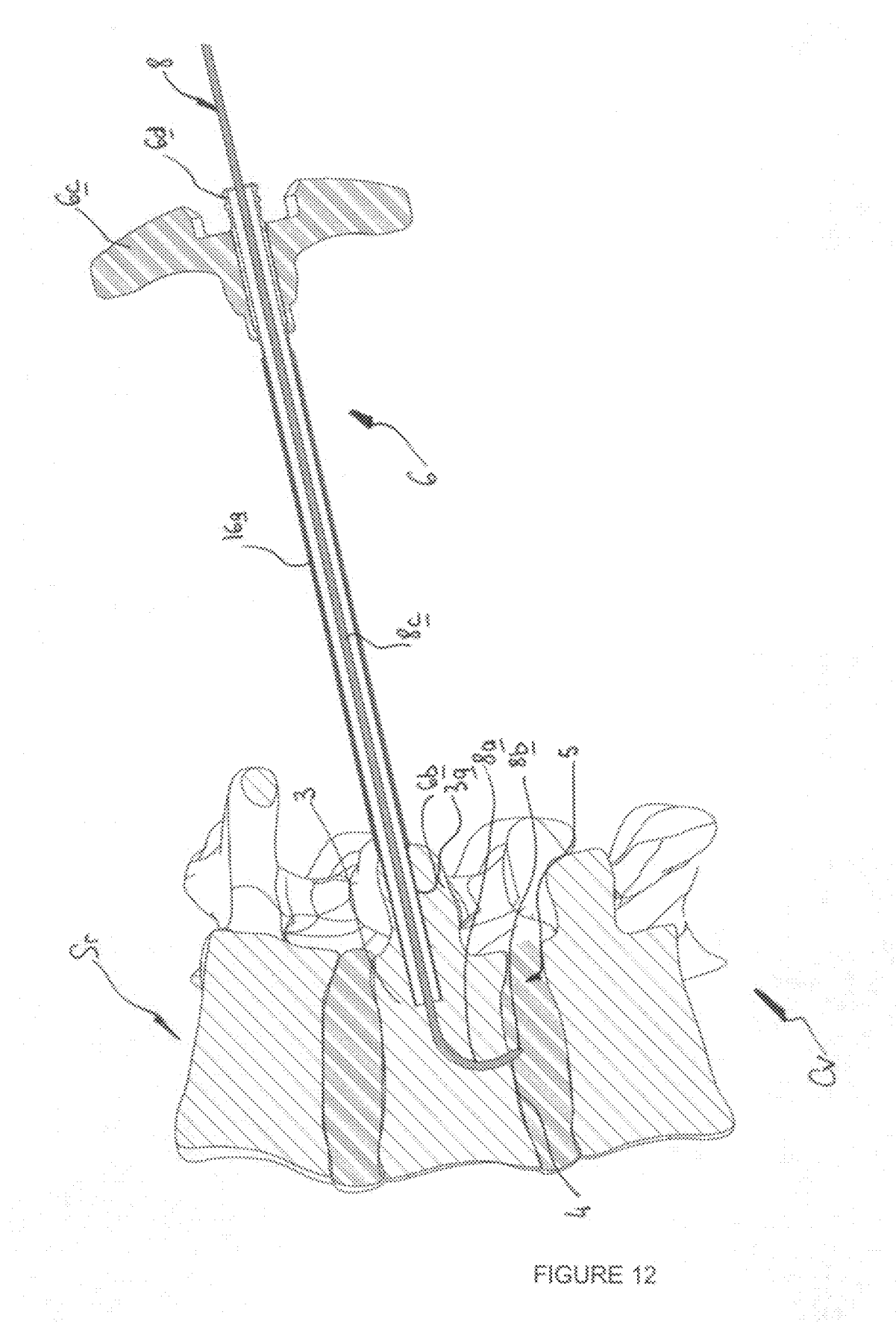

The tensioning screw 9e of the pin holder 9 is unlocked so as to allow said pin holder to be retracted from the straight cannula 6, leaving the guide pin 8 in the vertebra 3 and inside said straight cannula 6 (FIG. 12).

The straight cannula 6 is then unscrewed slightly from the vertebral body 3 to leave in the spongy bone a free portion of the straight osseous channel 2a in the extension of the tube 6a of said cannula (FIG. 13).

FIGS. 14 to 20 show the different stages of insertion of the articulated drill bit 10 of the drilling device 1, making it possible to form a curved channel 2b in the vertebral body of a vertebra 3 in order to reach the upper face of the intervertebral disc 5.

Figure 14:
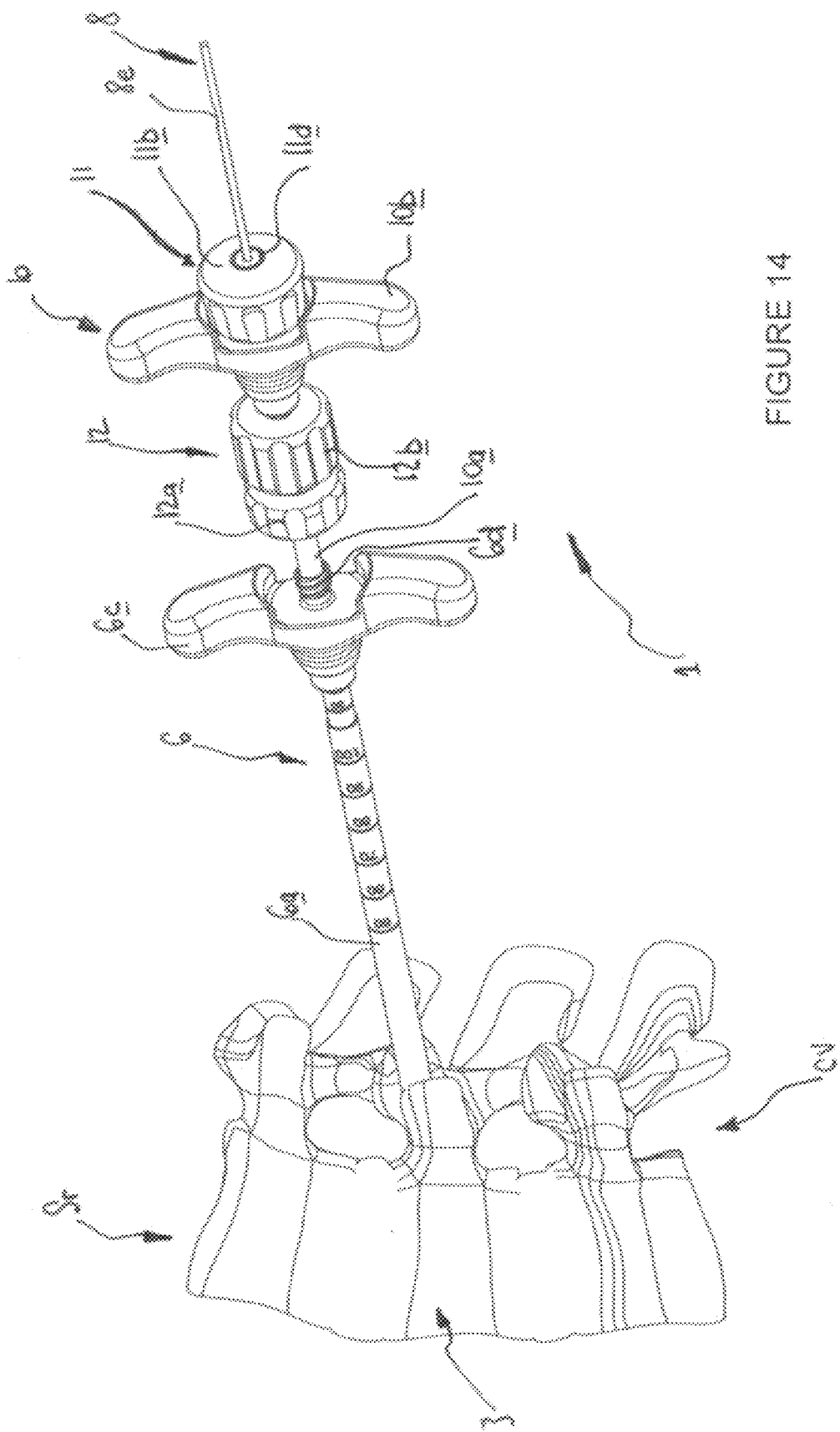
FIGS. 14 to 20 show the different steps making it possible to form a curved channel in the vertebral body of a vertebra in order to reach the upper face of the intervertebral disc using an articulated drill bit of the drilling device according to the present invention.
Figure 15:
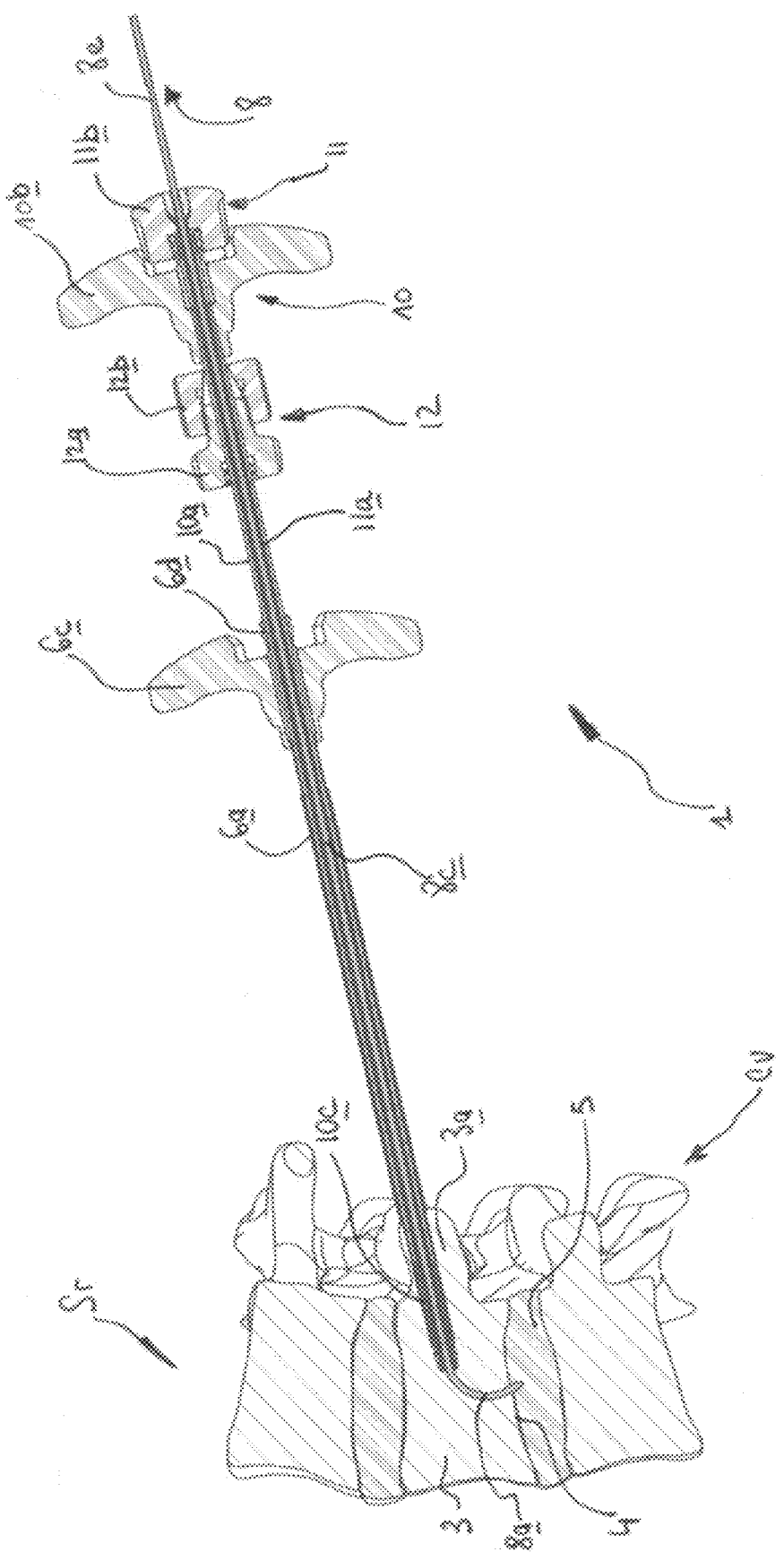

The centering sheath 11 is inserted inside the metal tube 10a of the articulated drill bit 10 so its grasping head 11b is screwed onto the cylindrical sleeve 10j of the grip 10b of said articulated drill bit (FIGS. 14 and 15).

The locking device 12 formed of the retaining element 12a and the fixing nut 12b is placed around the metal tube 10a of the articulated drill bit 10, just below the grasping grip 10b (FIGS. 14 and 15).

The articulated drill bit 10 equipped with its centering sheath 11 and its locking device 12 is inserted into the cylindrical tube 6a of the straight cannula 6 so the guide pin 8 is placed inside the plastics material tube 11a of said sheath which is arranged in the metal tube 10a of said drill bit (FIGS. 14 and 15).

The metal tube 10a of the articulated drill bit 10 is guided as far as the end of the straight channel 2a formed in the spongy bone of the body of the vertebra 3 in such a way that the sets of teeth 10e and 10g are in contact with said spongy bone (FIG. 15).

The metal tube 10a is then rotated and moved in translation via a pushing action by means of the grasping grip 10b inside the straight cannula 6, in such a way that the sets of teeth 10e and 10g penetrate inside the spongy bone of the vertebra 3. The displacement of the articulated drill bit 10 is guided inside the spongy bone via the guide pin 8 so as to facilitate drilling of the curved channel 2b.

Figure 16:
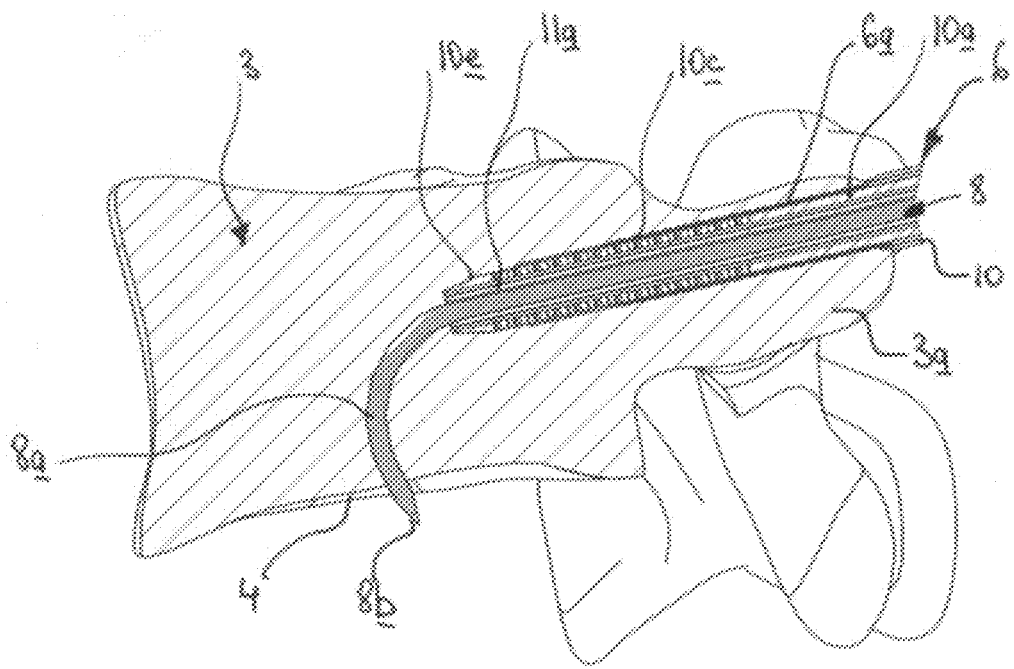
Figure 17:
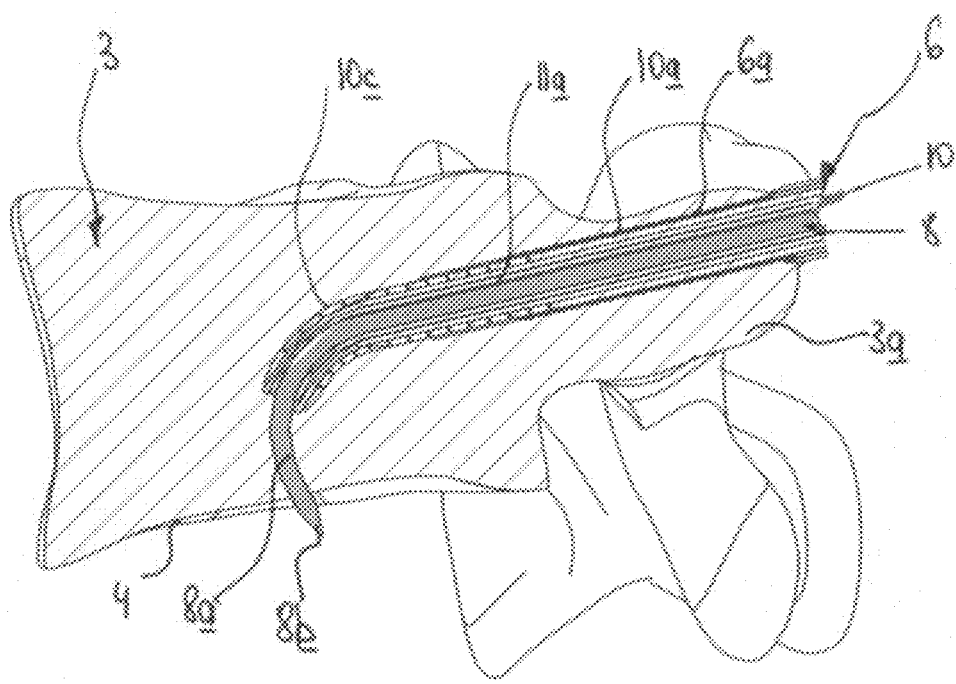
Figure 18:
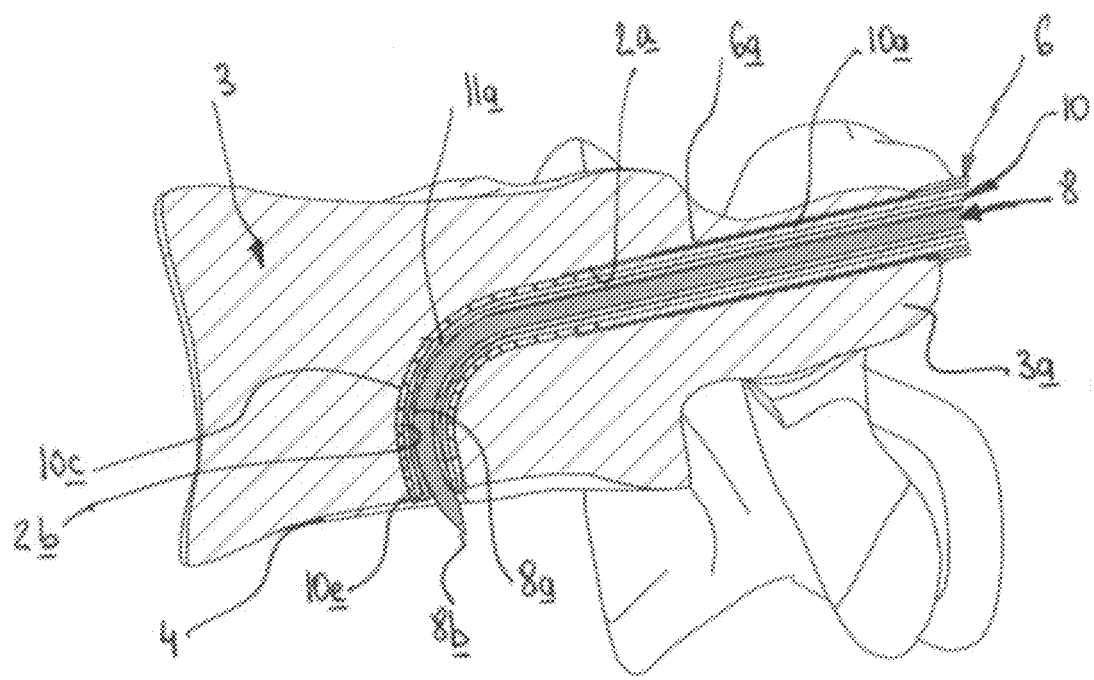

The articulated drill bit 10 deforms at its free end in accordance with the radius of curvature R of the guide pin 8 owing to the arrangement and the cuts made in the metal tube 10a constituting the profile 10c (FIGS. 16 to 18).

The articulated drill bit 10 enables drilling of the curved channel 2b inside the spongy bone of the vertebra 3 so as to open out in a direction substantially perpendicular to the level of the lower plateau formed by the cortical plateau 4 and thus above the intervertebral disc 5.

The adjustment of the articulated drill bit 10 so it emerges in the cortical plateau 4 in a substantially perpendicular direction and thus inside the intervertebral disc 5 is achieved by the dimensions of the radius of curvature R and the angle Y of the guide pin 8.

Figure 21:
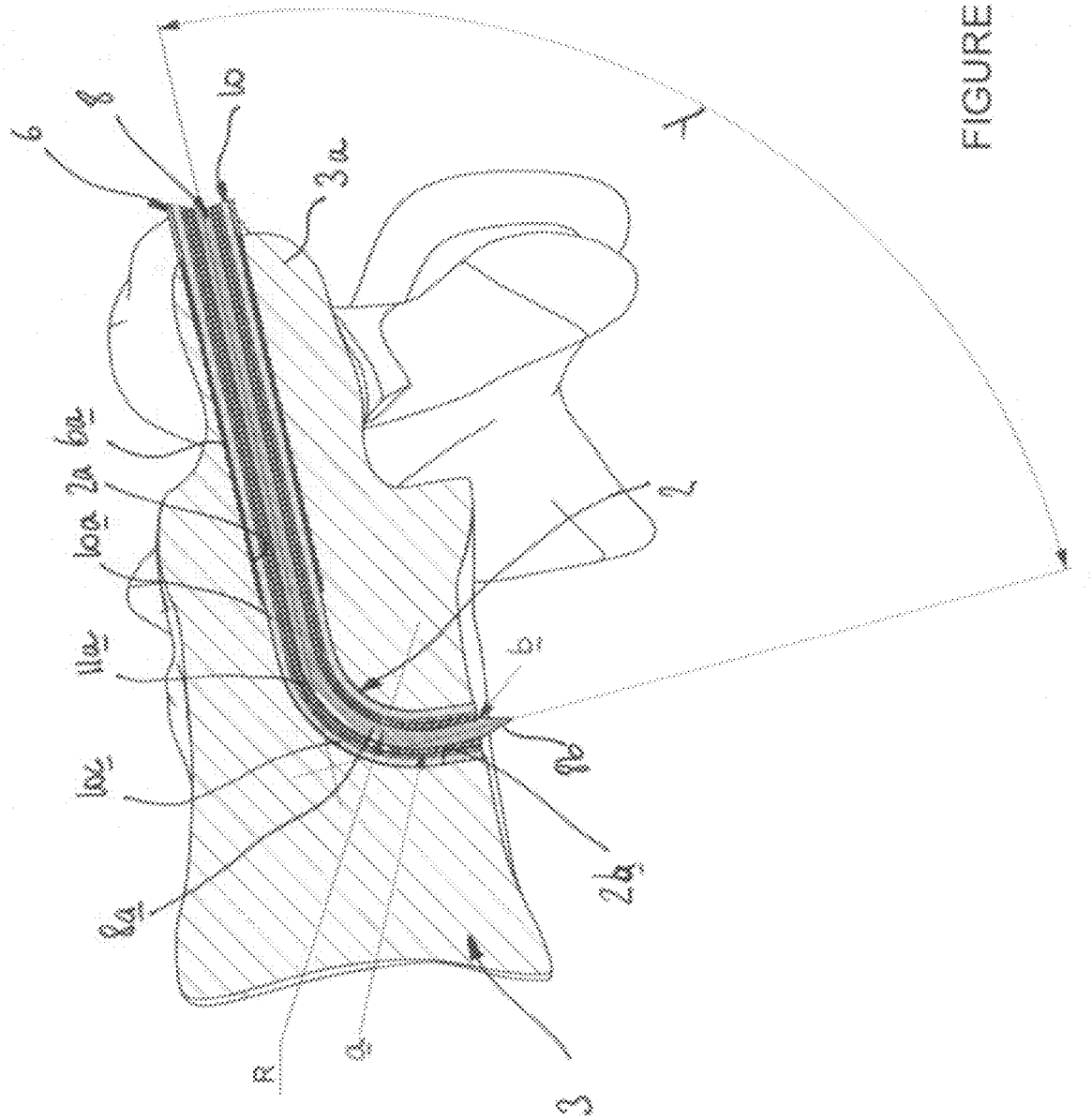
FIG. 21 shows the contact zones of the articulated drill bit relative to the guide pin of the drilling device according to the present invention making it possible to position the free end of said articulated drill bit in a direction substantially perpendicular to the plateau of the vertebra to be drilled.

For this, the radius of curvature R of the guide pin 8 makes it possible to define, after insertion of said guide pin into the vertebral body 3 and at the curved profile 8a thereof, two contact points a and b ensuring guidance of the free end 10c of the articulated drill bit 10 in order to position it during drilling in a direction substantially perpendicular to the cortical plateau 4 of the vertebra 3 to be drilled (FIG. 21).

The first contact point a is defined by the tangent to the outer profile of the radius of curvature R of the guide pin 8 which is perpendicular to the cortical plateau 4 of the vertebra 3, whereas the second contact point b is defined by the free end of the articulated drill bit 10 which rests against the inner profile of the sharpened tip 8b of the guide pin 8 arranged within the depth of the cortical plateau 4 of the vertebra 3 (FIG. 21).

Figure 19:
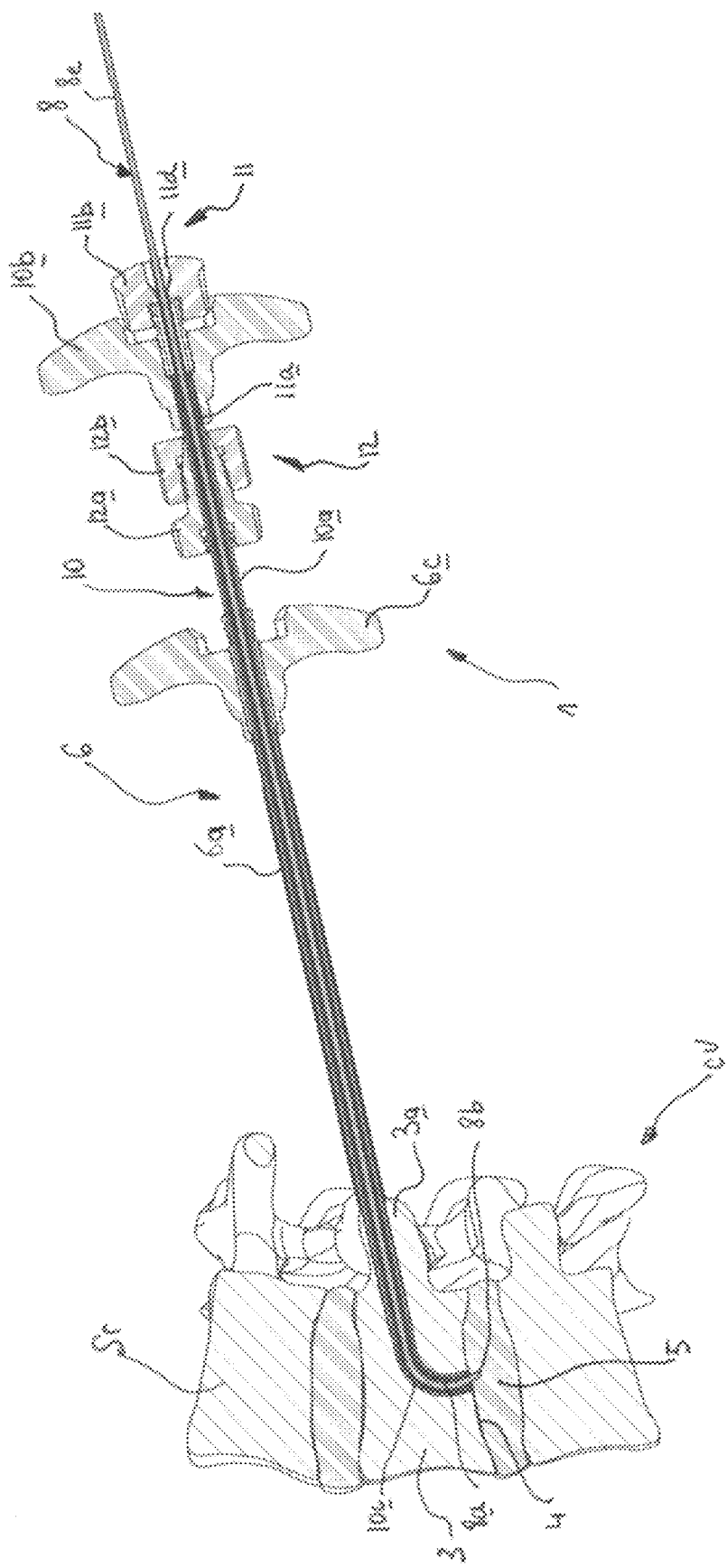

When the articulated drill bit 10 has drilled into the cortical plateau 4 of the vertebra 3, it is held in position and immobilised on the straight cannula 6 by means of the locking device 12. For this, the retaining element 12a is screwed onto the threaded profile 6d of the straight cannula 6, whereas the fixing nut 12b is screwed onto the retaining element 12a so as to immobilise the locking device 12 by pinching the metal tube 10a of the articulated drill bit 10 (FIGS. 19 and 20).

The locking of the articulated drill bit 10 on the straight cannula 6 makes it possible to avoid any displacement of said drill bit during extraction of the guide pin 8 and of the centering sheath 11 (FIG. 20).

As soon as the articulated drill bit 10 is released from the guide pin 8 and the centering sheath 11, it allows access via its inner curved channel to other instruments (not shown) which ensure, for example, nucleotomy of the intervertebral disc 5.

It should also be understood that the description above is given merely by way of example and in no way limits the scope of the invention, which will not be departed from by replacing any of the details described above with any other equivalent.

The invention claimed is:

1. A drilling system for forming an osseous channel with a curved profile via a straight cannula previously fixed in a body of a vertebra with a cortical plateau of a spinal segment of a vertebral column, the drilling system comprising:
    an articulated drill bit; and
    a guide pin which is provided from a guide pin kit and has at one end i) a curved profile of which a radius of curvature is less than 20 millimeters, and ii) a sharpened tip arranged in a direction defined by an angle which is less than 90 degrees to a longitudinal axis of the pin, the profile of the guide pin defining, after insertion thereof into the body of the vertebra, first and second contact points ensuring guidance of a free end of the articulated drill bit, the guide pin being configured to receive the articulated drill bit over an outer surface of the guide pin, and to guide the articulated drill bit and cause the articulated drill bit to deform,
    wherein the articulated drill bit is configured to deform at the free end thereof in accordance with the radius of curvature of the guide pin as the articulated drill bit is guided along the guide pin,
    the guide pin is configured to position the free end of the articulated drill bit in a direction substantially perpendicular to that of the cortical plateau of the vertebra to be drilled,
    the articulated drill bit is formed of a metal cylindrical tube comprising
        a grasping grip at one end thereof, and
        a profile at the other end thereof, the other end being cropped, the profile ensuring deformation and articulation of the other end in a curved shape, so as to define a cutting end comprising
            a first set of teeth arranged over a periphery of the tube, and
            a second set of teeth arranged at the other end of the metal tube and a protective sheath arranged in an inner portion of the metal tube, the protective sheath being made of a resilient material to internally smooth irregularities and gaps in the free end arising from the profile.

2. The drilling system according to claim 1, wherein the first contact point is defined by a tangent to the outer profile of the radius of curvature of the guide pin which is perpendicular to the cortical plateau of the vertebra, and the second contact point is defined by the free end of the articulated drill bit which rests against an inner profile of the sharpened tip of the guide pin arranged within a depth of the cortical plate of the vertebra.

3. The drilling system according to claim 1, wherein the guide pin is made of a material which is both hard-wearing and flexible.

4. The drilling system according to claim 1, wherein the guide pin has an outer diameter which is less than 3 millimeters.

5. The drilling system according to claim 4, wherein the guide pin has an outer diameter which is between 1.4 millimeters and 2 millimeters.

6. The drilling system according to claim 1, wherein the curved profile has a radius of curvature which is between 10 millimeters and 20 millimeters.

7. The drilling system according to claim 1, wherein the angle of the sharpened tip is between 70 and 85 degrees with respect to the longitudinal axis of the guide pin.

8. The drilling system according to claim 1, wherein the guide pin comprises a straight longitudinal portion having a flattened part which cooperates with a complementary profile formed in a pin holder, ensuring i) that the guide pin is blocked against rotation inside the pin holder, and ii) that the guide pin is rigidified over the straight longitudinal portion during insertion of the guide pin and of the pin holder through the straight cannula previously fixed in the body of the vertebra.

9. The drilling system according to claim 8, wherein the guide pin comprises a notch formed in the straight longitudinal portion beside the flattened part at the end opposite the end with the curved profile of the guide pin, the notch cooperating with a tensioning screw which is guided in a grasping grip of the pin holder to block movement in translation of the guide pin in the pin holder.

10. The drilling system according to claim 8, wherein the pin holder is formed of a metal cylindrical tube formed in one piece at one end thereof with a grasping grip equipped with a tensioning screw and a hollow cylindrical sleeve having, over an outer profile thereof, a fast thread adapted to screw in a plug to block the movement in translation of the guide pin relative to the pin holder.

11. The drilling system according to claim 1, wherein the grasping grip comprises a hollow cylindrical sleeve in an extension of the metal tube, the sleeve having, over an outer profile thereof, a fast thread to insert and fix a centering sheath inside the metal tube.

12. The drilling system according to claim 11, wherein the centering sheath is formed of a cylindrical tube made of a resilient material and formed in one piece at one end thereof with a grasping head comprising
  an inner threaded bore for cooperation with the sleeve of the grip of the articulated drill bit for immobilization of the sleeve on the articulated drill bit, and
  a blocking device opposite the inner threaded bore blocking movement in translation of the cylindrical tube inside grasping head of the centering sheath.

13. The drilling system according to claim 11, wherein the articulated drill bit comprises a locking device arranged on the metal tube and beneath the grasping grip so as to immobilize the drill by a retaining element and a fixing nut on the straight cannula previously fixed in the body of the vertebra.

14. The drilling system according to claim 13, wherein the locking device is formed of a retaining element comprising a cylindrical head formed in one piece with a sleeve having a cylindrical outer profile equipped with a thread extending via a split, conical outer profile.

15. The drilling system according to claim 14, wherein the retaining element is perforated through a middle thereof by a through-bore comprising an inner thread at the cylindrical head cooperating with a threaded profile of the straight cannula in order to immobilize the retaining element over the cannula.

16. The drilling system according to claim 14, wherein the locking device is formed of a fixing nut comprising
  a first threaded bore in an inner portion of the fixing nut, the first threaded bore cooperating with the thread formed in the cylindrical portion of the sleeve of the retaining element, and
  a second inner bore which is coaxial with the first inner bore and has a conical inclination profile complementary to the conical outer profile of the sleeve.

17. The drilling system according to claim 1, wherein the protective sheath ensures a significant coefficient of slip for sliding of the guide pin and/or of a centering sheath during drilling of the osseous channel with the curved profile.

18. The drilling system according to claim 1, wherein the profile of the metal cylindrical tube is formed of a sequence of alternately concave and convex loops ensuring deformation and articulation of the end of the articulated drill bit in a curved shape.

19. The drilling system according to claim 1, wherein a cutting edge of each tooth of the first set of teeth is slightly inclined relative to the longitudinal axis of the articulated drill bit.

20. The drilling system according to claim 1, wherein a cutting edge of each tooth of the second set of teeth is sharply inclined so as to intersect the longitudinal axis of the articulated drill bit.

21. The drilling system according to claim 1, wherein the articulated drill bit comprises safety means ensuring recovery of the cutting end when the articulated drill bit breaks.

22. The drilling system according to claim 21, wherein the safety means are formed by a resilient thread or wire arranged inside the metal tube and between an inner face of the tube and the protective sheath in such a way that each end of said resilient thread cooperates with a grasping head of the centering sheath.

23. The drilling system according to claim 21, wherein the safety means are formed by a resilient thread or wire arranged inside the metal tube and between the protective sheath, which is formed in one piece with an inner face of the tube, and an outer face of a centering sheath in such a way that each end of the resilient thread cooperates with a grasping head of the centering sheath.

24. The drilling system according to claim 23, wherein the ends of the resilient safety thread respectively comprise a stop arranged in a seat of similar profile formed in the grasping head of the centering sheath.

* * * * *